US010765809B2

(12) United States Patent
Bechmann et al.

(10) Patent No.: US 10,765,809 B2
(45) Date of Patent: Sep. 8, 2020

(54) AUTO-INJECTOR FOR EPINEPHRINE INJECTION

(71) Applicant: MERCK PATENT GMBH, Darmstadt (DE)

(72) Inventors: Soeren Bechmann, Holstebro (DK); Flemming Madsen, Aalborg SV (DK); Esben Johansen, Struer (DK)

(73) Assignee: MERCK PATENT GMBH, Darmstadt (DE)

(*) Notice: Subject to any disclaimer, the term of this patent is extended or adjusted under 35 U.S.C. 154(b) by 147 days.

(21) Appl. No.: 15/622,812

(22) Filed: Jun. 14, 2017

(65) Prior Publication Data

US 2017/0348487 A1 Dec. 7, 2017

Related U.S. Application Data

(63) Continuation of application No. 14/852,109, filed on Sep. 11, 2015, now Pat. No. 9,764,091, which is a
(Continued)

(51) Int. Cl.
*A61M 5/20* (2006.01)
*A61M 5/32* (2006.01)
(Continued)

(52) U.S. Cl.
CPC ........ *A61M 5/2033* (2013.01); *A61M 5/3204* (2013.01); *A61M 5/326* (2013.01);
(Continued)

(58) Field of Classification Search
CPC ............... A61M 5/20; A61M 5/31525; A61M 5/31526; A61M 5/31528; A61M 5/3153;
(Continued)

(56) References Cited

U.S. PATENT DOCUMENTS 5,092,842 A * 3/1992 Bechtold ................. A61M 5/20
604/135
5,114,406 A 5/1992 Gabriel
(Continued)

FOREIGN PATENT DOCUMENTS

CN 1849148 A 10/2006
CN 101925374 A 12/2010
(Continued)

OTHER PUBLICATIONS

International Search Report in PCT/EP2018/062822 dated Jul. 25, 2018 (pp. 1-18).
(Continued)

*Primary Examiner* — Kami A Bosworth
(74) *Attorney, Agent, or Firm* — Millen, White, Zelano & Branigan, P.C.; William Nixon

(57) ABSTRACT

A reloadable auto injector has a needle insertion driver to be re-activated upon reloading. A syringe is movably positioned in a housing between a first position and a second position. A plunger rod is locked to a plunger rod tube by a deflectable locking member. A syringe driver applies a force to the syringe to move the syringe together with plunger rod tube, plunger rod and plunger rod driver from the first position to the second position. In the second position, the locking member is unlocked and releases the plunger rod to thereby activate the plunger rod driver to advance the plunger rod in the syringe for delivering of medicament. A reload handle is connected to the syringe assembly so that user operation of the reload handle retracts the syringe to the first position and simultaneously reloads the syringe driver for delivering a further dose of medicament.

16 Claims, 17 Drawing Sheets

Related U.S. Application Data continuation of application No. 14/344,019, filed as application No. PCT/IB2012/002278 on Sep. 10, 2012, now Pat. No. 9,186,459.

(60) Provisional application No. 61/532,892, filed on Sep. 9, 2011.

(51) Int. Cl.
    *A61M 5/00*     (2006.01)
    *A61M 5/315*     (2006.01)

(52) U.S. Cl.
CPC ............ *A61M 5/002* (2013.01); *A61M 5/3157* (2013.01); *A61M 2005/202* (2013.01); *A61M 2005/206* (2013.01); *A61M 2005/2013* (2013.01); *A61M 2005/3267* (2013.01); *A61M 2205/581* (2013.01); *A61M 2205/583* (2013.01)

(58) Field of Classification Search
CPC .......... A61M 5/13568; A61M 5/31593; A61M 5/31595; A61M 2005/2013; A61M 2005/202; A61M 2005/206; A61M 2005/2073; A61M 2005/208; A61M 5/2422; A61M 5/281; A61M 5/31568
See application file for complete search history.

(56) References Cited

U.S. PATENT DOCUMENTS

| | | | |
|---|---|---|---|
| 5,320,609 A | 6/1994 | Haber | |
| 5,540,664 A * | 7/1996 | Wyrick | A61M 5/002 604/135 |
| 5,643,214 A | 7/1997 | Marshall | |
| 5,695,472 A * | 12/1997 | Wyrick | A61M 5/002 604/135 |
| 6,210,369 B1 | 4/2001 | Wilmot | |
| 6,241,709 B1 * | 6/2001 | Bechtold | A61M 5/2033 604/207 |
| 6,454,743 B1 | 9/2002 | Weber | |
| 7,465,289 B2 | 12/2008 | Marshall | |
| 7,749,195 B2 | 7/2010 | Hommann | |
| 7,976,499 B2 | 7/2011 | Grunhut | |
| 8,088,111 B2 | 1/2012 | Cowe | |
| 8,348,905 B2 | 1/2013 | Radmer | |
| 8,376,998 B2 | 2/2013 | Daily | |
| 8,425,460 B2 | 4/2013 | Cowe | |
| 8,568,359 B2 | 10/2013 | Carrel | |
| 8,708,968 B2 | 4/2014 | Julian | |
| 8,808,244 B2 | 8/2014 | Adlon | |
| 8,870,827 B2 | 10/2014 | Young | |
| 8,992,484 B2 | 3/2015 | Radmer | |
| 9,192,731 B2 | 11/2015 | Roberts | |
| 9,242,053 B2 | 1/2016 | Wozencroft | |
| 9,345,831 B2 | 5/2016 | Raday | |
| 9,764,091 B2 | 9/2017 | Bechmann | |
| 9,775,948 B2 | 10/2017 | Bechmann | |
| 2001/0005781 A1 | 6/2001 | Bergens | |
| 2003/0105430 A1 | 6/2003 | Lavi | |
| 2005/0101919 A1 | 5/2005 | Brunnberg | |
| 2005/0277885 A1 | 12/2005 | Scherer | |
| 2006/0069354 A1 | 3/2006 | Buenger | |
| 2006/0173408 A1 * | 8/2006 | Wyrick | A61M 5/2033 604/110 |
| 2006/0189933 A1 | 8/2006 | Alheidt | |
| 2007/0017533 A1 * | 1/2007 | Wyrick | A61M 5/2033 128/898 |
| 2008/0009807 A1 | 1/2008 | Hommann | |
| 2008/0058732 A1 | 3/2008 | Harris | |
| 2008/0228147 A1 | 9/2008 | David-Hegerich | |
| 2008/0262438 A1 | 10/2008 | Bollenbach | |
| 2009/0270804 A1 | 10/2009 | Mesa | |
| 2010/0137808 A1 | 6/2010 | Wilmot | |
| 2010/0268170 A1 | 10/2010 | Carrel | |
| 2011/0034878 A1 | 2/2011 | Radmer | |
| 2011/0137247 A1 | 6/2011 | Mesa et al. | |
| 2011/0202011 A1 | 8/2011 | Wozencroft | |
| 2011/0213314 A1 | 9/2011 | Guillermo | |
| 2012/0046609 A1 | 2/2012 | Mesa | |
| 2012/0130342 A1 | 5/2012 | Cleathero | |
| 2012/0310172 A1 | 12/2012 | MacDonald | |
| 2013/0060231 A1 | 3/2013 | Adlon | |
| 2013/0226085 A1 | 8/2013 | Roberts | |
| 2013/0281938 A1 | 10/2013 | Ekman | |
| 2014/0257193 A1 | 9/2014 | Boström | |
| 2014/0323982 A1 | 10/2014 | Lumme | |
| 2014/0364805 A1 | 12/2014 | Llewellyn-Hyde | |
| 2015/0250953 A1 | 9/2015 | Elmén | |
| 2016/0022914 A1 | 1/2016 | Mounce | |

FOREIGN PATENT DOCUMENTS

| | | |
|---|---|---|
| CN | 102137691 A | 7/2011 |
| EP | 2311510 B1 | 5/2014 |
| EP | 2007450 B1 | 12/2014 |
| EP | 3061478 A1 | 8/2016 |
| GB | 2463034 A | 3/2010 |
| GB | 2467637 A | 8/2010 |
| JP | 2002508225 A | 3/2002 |
| JP | 2007504867 A | 3/2007 |
| JP | 2011509783 A | 3/2011 |
| WO | 2000024441 A1 | 5/2000 |
| WO | 2005023342 A1 | 3/2005 |
| WO | 2007129324 A1 | 11/2007 |
| WO | 2009092807 A1 | 7/2009 |
| WO | 2010049239 A1 | 5/2010 |
| WO | 2011039212 A1 | 4/2011 |
| WO | 2013028906 A1 | 2/2013 |
| WO | 2013032389 A1 | 3/2013 |
| WO | 2013034984 A2 | 3/2013 |
| WO | 2013034986 A2 | 3/2013 |
| WO | 2014056874 A1 | 4/2014 |
| WO | 2016075254 A1 | 5/2016 |

OTHER PUBLICATIONS

International Search Report in PCT/EP2018/062821 dated Dec. 13, 2018 (pp. 1-26).
International Search Report for PCT/IB2012/002247 dated Jun. 4, 2013.
Third Party Observations related to European Patent Application No. 12816495.1, filed Sep. 10, 2012.
International preliminary report on Patentability in PCT/IB2012/002267 dated Mar. 12, 2014.
First Office Action in corresponding CN application No. 201280043854 dated Jul. 3, 2015.
Office Action in corresponding JP Application 2014-529086 dated Aug. 1, 2016.
Office Action in co-pending U.S. Appl. No. 14/343,881, dated Mar. 9, 2017.
Translation of Office Action (pp. 1-6) and Search Report (pp. 1-3) in corresponding CN appl. No. 201610571453.9 dated Dec. 7, 2018.

\* cited by examiner

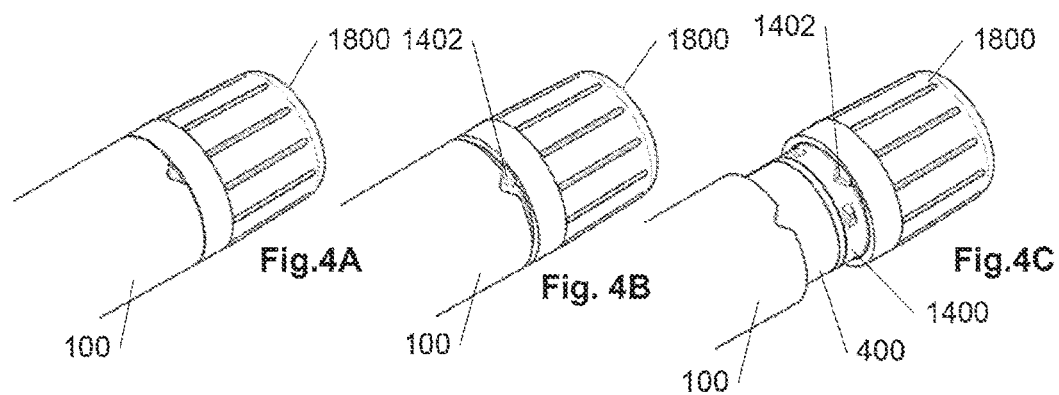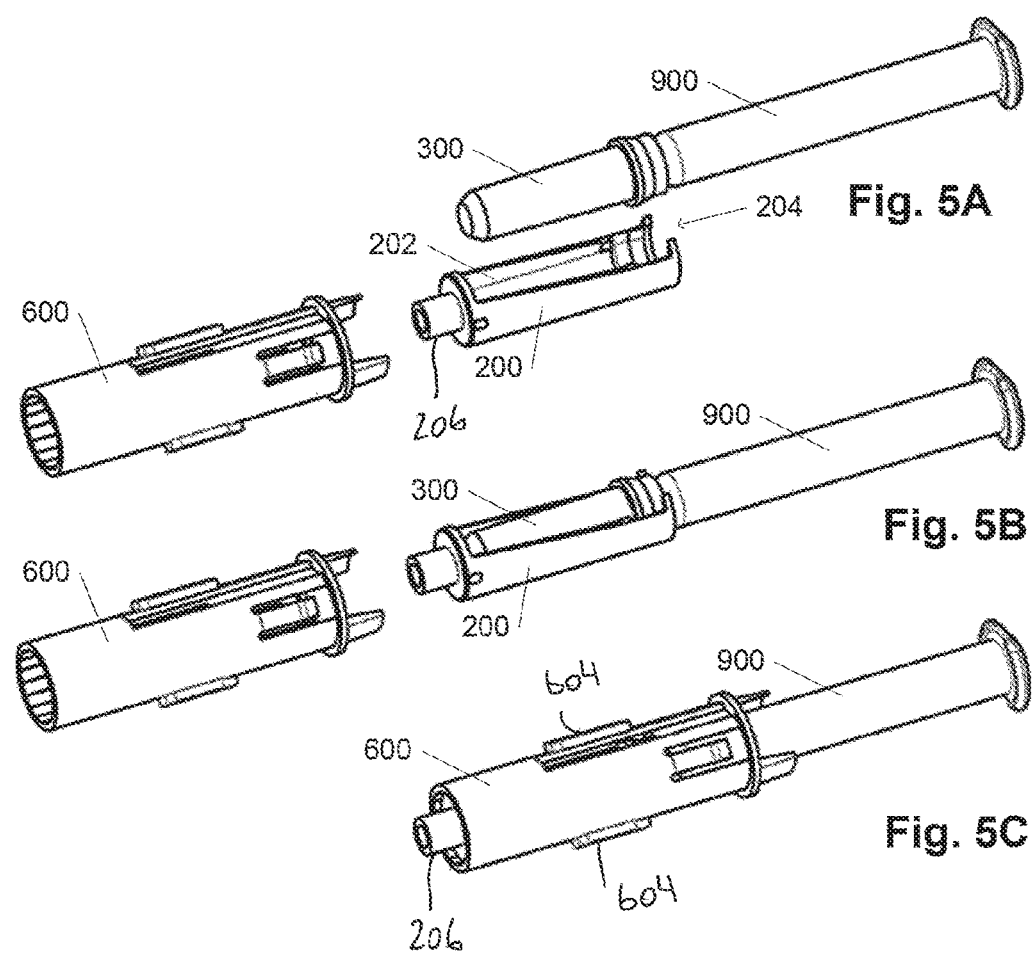

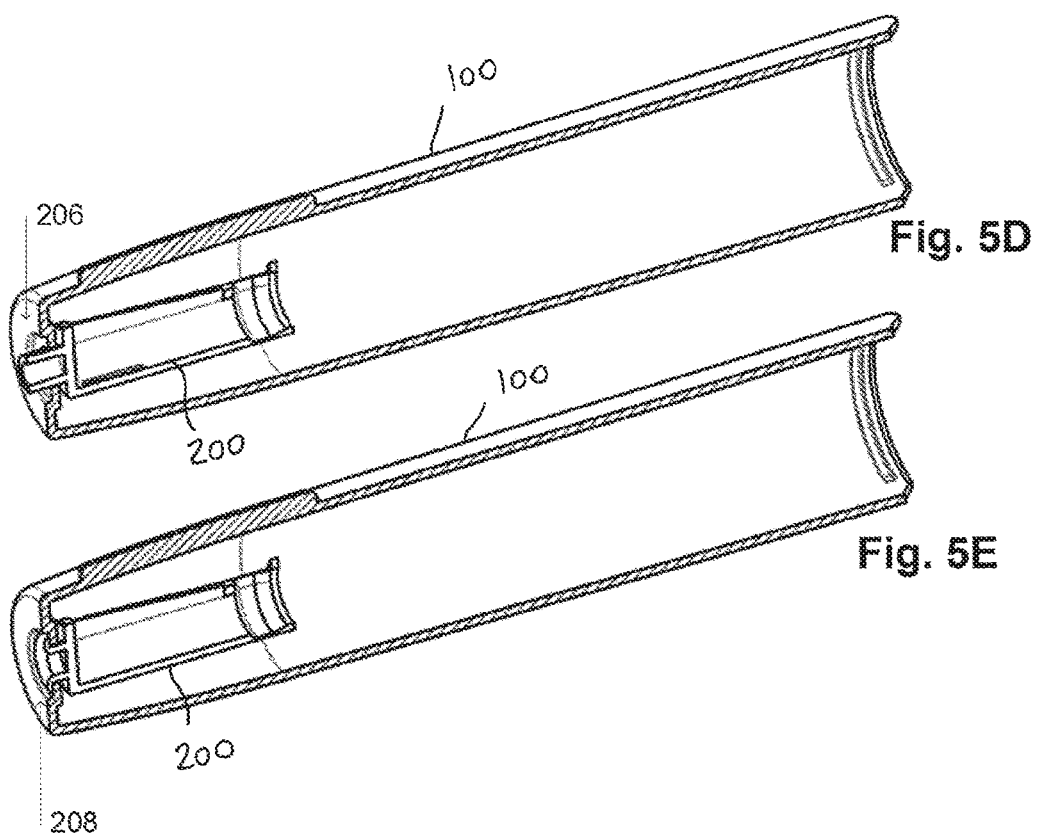

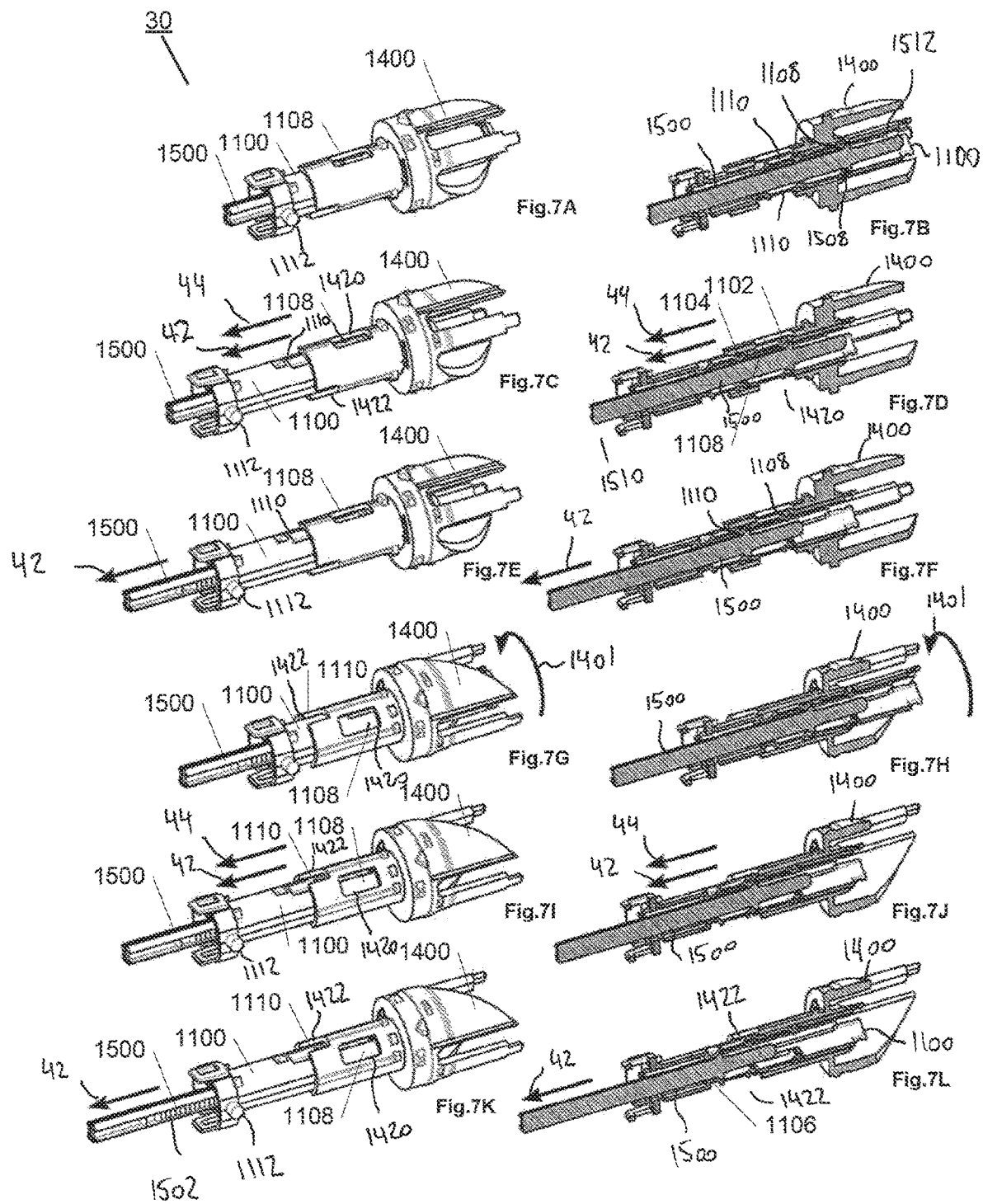

AUTO-INJECTOR FOR EPINEPHRINE INJECTION

TECHNICAL FIELD

The present invention relates to auto injectors, such as medical auto injectors, and especially to reloadable auto injectors which may be capable of delivering one or more individual doses from a medicinal cartridge or a pre-filled syringe containing medicine wherein the reload of the auto injector may require a clear operator input to allow for a delivering a further dose. The auto injectors may be configured for single or multi-use.

BACKGROUND OF THE INVENTION

Auto injectors are well-known in the art, and are often preferred by users for self administration of medicine, such as for subcutaneous injection of medicines such as insulin, medicine to treat or alleviate multiple sclerosis, rheum, lupus, etc. or for emergency injection of e.g. adrenaline or epinephrine, such as injection in to muscle tissue.

The needles used for injection subcutaneously and for injection into muscle tissue are typically of different lengths. Typically, needles used for subcutaneous injections are about 12 mm ("half-inch") whereas needles used for injection into muscle tissue may have a length of 20-25 mm ("inch"), to ensure that muscle tissue is reached.

The selected needle bore may also affect the degree of patient discomfort during injection. Smaller bore diameters, typically provide more patient comfort, whereas larger bore diameters enable more rapid delivery of the liquid through the needle and with a lower force. A compromise is therefore needed in selecting needle bore to provide acceptable patient comfort and liquid delivery through the needle characteristics.

Allergic reactions tend to become an ever increasing problem and for the treatment of severe allergic reactions (anaphylaxis) to foods, insect stings or bites, drugs and other allergens, as well as idiopathic or exercise induced anaphylaxis, adrenaline or epinephrine is typically used.

Epinephrine works quickly to reverse the symptoms of an anaphylactic reaction and epinephrine injected into the muscle of the front of the upper outer thigh is typically used for the emergency treatment of anaphylaxis.

Typically, epinephrine auto-injectors are single use injectors for injecting a pre-measured single dose of epinephrine for the emergency treatment of anaphylaxis.

However, when administering some drugs, such as epinephrine, a single dose may not be sufficient to treat the anaphylaxis. In order for one patient to be able to receive full treatment including one, two or more doses with a single injector, different auto injectors have been suggested.

Different possibilities for the injection of two doses from a same syringe have been suggested and in U.S. Pat. No. 7,927,303 and EP700307, two-dose auto injectors are disclosed allowing the automatic delivering of a first dose of a medicament and the manual refitting of the auto injector so that the once used syringe may be re-inserted into the auto injector for administration of a second dose.

In WO 2011/111006, an auto injector is disclosed in which the locking and releasing of the drive spring of the auto injector is controlled by providing stepped guide means with ramps for two successive slidings there along of slide means operated by the spring and connected with the syringe and relevant plunger. Thus, after a first dose has been delivered, a further dose may be delivered using the same spring and slide the syringe further along the slide means.

It is a disadvantage of the disclosed auto injector that the length of the device increases significantly when a second dose is delivered.

Furthermore, auto injectors have been disclosed focusing on reducing the risk of wet injection. For example, WO 2012/045827 discloses an auto injector having an arrangement for coupling a plunger rod to either a syringe or a stopper arranged in the syringe. However, it is a disadvantage of the auto injector as disclosed that a single compression spring is applied for injecting the needle and for injecting the medicament, in that the resistance of the needle penetrating the skin may tend to force the syringe backwards in a syringe carrier, whereby the stopper may contact the forward moving plunger rod and expelling the medicament prematurely which may result in a wet injection.

U.S. Pat. No. 7,785,292 discloses an auto injector comprising a housing wherein a single driving mechanism is used to insert the needle and to inject the medicament. The syringe is moved to a forward position before the piston is allowed to move forward to inject the medicament. A locking mechanism engages the drive with the syringe when the syringe is not in the forward position and engages the syringe with the housing when the syringe is in the forward position.

The prior art documents thus disclose the use of a single drive mechanism, the engagement of which is shifted depending on the position of the syringe.

There is therefore a need for an auto injector which allows for selectively delivery of one or more doses, wherein subsequent doses are also delivered automatically and which is both compact in size and highly robust with respect to the avoidance of wet injections.

SUMMARY OF INVENTION

It is an object of the present invention to provide a reloadable auto-injector having separate needle insertion and medicament injection overcoming one or more of the disadvantages of the prior art.

In one aspect of the present invention a reloadable auto injector for adrenaline injection is provided. The auto injector may have a housing for accommodation of a syringe with a needle, and the syringe may be movably positioned in the housing between a first position in which position the needle is accommodated inside the housing and a second position in which position the needle protrudes outside the housing. The housing may further accommodate a plunger rod configured to be advanced in the syringe for delivering at least one dose of medicament, and a plunger rod tube. The plunger rod tube may have two or more deflectable locking members configured to interact with a plunger rod stop to normally lock the plunger rod to the plunger rod tube. A syringe driver may be configured to apply a force to the syringe thereby moving the syringe from the first position to the second position, and the syringe driver may be further configured to advance the plunger rod tube with the plunger rod to the second position. Preferably, the syringe driver moves the plunger rod tube and the plunger rod concurrently with the syringe. A plunger rod driver may be configured to apply a force to the plunger rod to advance the plunger rod in the syringe for delivering one dose of medicament upon unlocking of each of the two or more deflectable locking members. The auto injector may further comprise a reload mechanism configured to retract the syringe from the second position to the first position and reload the syringe driver to allow a repeated activation of the syringe driver. The reload mechanism may be configured to unlock a first deflectable locking member upon a first movement of the syringe from the first position to the second position to thereby release the plunger rod from the plunger rod tube for delivering a first dose of medicament, and unlock a further deflectable locking member upon a further movement of the syringe from the first position to the second position to thereby release the plunger rod from the plunger rod tube for delivering a further dose of medicament.

According to another aspect of the present invention, a reloadable auto injector for epinephrine injection is provided. The reloadable auto injector may comprise a separate needle insertion driver and medicine injection driver wherein needle insertion driver is configured to be re-activated upon reloading.

It is an advantage of the present invention that the auto injector may be used to deliver one or more doses of medicament, depending on the user or patient operation of the auto injector. Thus, one or more individual doses may be delivered from e.g. a medicinal cartridge or pre-filled syringe containing medicine. It is an advantage of the present invention that a clear operator or patient input is required in order to allow an additional dose to be delivered. The operator input may comprise operating a reload mechanism, and the reload mechanism may comprise activating the auto injector for a further injection.

It is an advantage of the above described auto injectors that the mechanism is fully reversible. Thereby, any sharps protection in the form of a skin sensor or the like may be locked in the intermediate position, i.e. after a first dose is delivered and before the auto injector is reloaded. Thereby, the patient and/or the operator is protected against the needle also in between dose deliveries. It is especially for the acute treatment of e.g. allergies, advantageous that the needle shield may be locked after the first dose delivery or first dose injection, as the patient may not need a further treatment and thus discard or re-use the auto injector after the first dose delivery. Thus, to safely dispose of the auto injector or the syringe assembly, the skin sensor may advantageously shield the needle after a dose has been delivered and may furthermore be locked in the forward position immediately following a dose delivery.

It is a further advantage of the present invention that the auto injector has a compact size in that the syringe assembly and the needle shield is retracted upon reload of the device, thereby limiting the length of the device.

It is furthermore advantageous to provide syringe driver and plunger rod driver as separate driving means in that the risk of wet injection, i.e. liquid medicament leaking out of the needle during needle insertion, is reduced.

The present invention may provide an auto injector which enables a patient to have at least two individual injections from one single syringe, and the patient or operator may apply similar steps to perform the first, second and any further injection. The patient or operator may have to activate the auto injector to enable a second or further injection or delivery of medicament.

In one or more embodiments of the present invention, a reloadable auto-injector with a housing for accommodation of a syringe assembly is provided. The syringe assembly may comprise a syringe with a needle, and the syringe assembly may be movably positioned in the housing between a first position in which position the needle is accommodated inside the housing and a second position in which position the needle protrudes outside the housing. The syringe assembly may further comprise a plunger rod configured to be advanced in the syringe for delivering at least one dose of medicament, and a plunger rod driver being configured to apply a force to the plunger rod to advance the plunger rod in the syringe for delivering at least one dose of medicament. Furthermore, a syringe driver may be accommodated inside the housing and be configured to apply a force to the syringe assembly thereby moving the syringe from the first position to the second position. The housing may still further comprise a reload handle configured to reload the auto injector for injecting a further dose of medicament, wherein the reload handle may be connected to the syringe assembly so that user or patient operation of the reload handle is configured to retract the syringe assembly to the first position and to simultaneously reload the syringe driver to thereby ready the auto injector for delivering a further dose of medicament. A syringe stopper may be movably positioned in the syringe and sealing syringe content and the plunger rod may be configured to engage the syringe stopper.

In some embodiments of the present invention, a reloadable auto-injector with a housing for accommodation of a syringe assembly comprising a syringe with a needle is provided. The syringe assembly may be movably positioned in the housing between a first position in which position the needle is accommodated inside the housing and a second position in which position the needle protrudes outside the housing. The syringe assembly may further comprise a plunger rod driver being configured to apply a force to a plunger rod to advance the plunger rod in the syringe for delivering at least one dose of medicament. The housing may furthermore accommodate a syringe driver configured to apply a force to the syringe assembly thereby moving the syringe from the first position to the second position and the auto injector further comprises a reload handle configured to reload the auto injector for injecting a further dose of medicament. The reload handle may be connected to the syringe assembly so that user or patient operation of the reload handle is configured to retract the syringe assembly to the first position and to simultaneously reload the syringe driver.

In one or more embodiments of the present invention, a reloadable auto-injector with a housing for accommodation of a needle shield and a syringe assembly is provided. The syringe assembly may comprise a syringe with a needle and a plunger rod driver being configured to apply a force to a plunger rod to advance the plunger rod in the syringe for delivering at least one dose of medicament. A syringe driver may be configured to apply a force to the syringe assembly thereby moving the syringe from a first position to a second position and a reload handle may be configured to reload the auto injector for delivering a further dose of medicament, wherein the reload handle is connected to the syringe assembly and the needle shield so that user or patient operation of the reload handle is configured to retract the syringe assembly to the first position and to simultaneously reload the syringe driver and release the needle shield.

In one or more embodiments of the present invention, a method of reloading an auto injector is provided, wherein a reloadable auto-injector has a housing for accommodation of a needle shield and a syringe assembly. The syringe assembly may comprise a syringe with a needle and a plunger rod driver being configured to apply a force to a plunger rod to advance the plunger rod in the syringe for delivering at least one dose of medicament. A syringe driver may be provided in the housing and configured to apply a force to the syringe assembly thereby moving the syringe from a first position to a second position in which position a dose may be delivered.

The auto injector may furthermore comprise a reload handle configured to reload the auto injector for delivering a further dose of medicament, wherein the method comprises operating the reload handle to retract the syringe assembly to the first position, reload the syringe driver and release the needle shield to thereby ready the auto injector for delivering a further second dose.

In one or more further embodiments of the present invention, a method of operating a reloadable auto injector is provided. The auto injector may comprise a housing for accommodation of a syringe assembly. The syringe assembly may comprise a syringe with a needle, and the syringe assembly may be movably positioned in the housing between a first position in which position the needle is accommodated inside the housing and a second position in which position the needle protrudes outside the housing. The syringe assembly may further comprise a plunger rod driver being configured to apply a force to a plunger rod to advance the plunger rod in the syringe for delivering at least one dose of medicament and the housing may further accommodate a syringe driver configured to apply a force to the syringe assembly thereby moving the syringe from the first position to the second position, a skin sensor for activation of the auto injector, a syringe lock for locking the syringe assembly in the first position, and a reload handle, wherein the method may comprises the steps of activating the skin sensor to rotate the syringe lock and release the syringe assembly, moving the syringe assembly from the first position to the second position, releasing the plunger rod driver to deliver a dose of medicament, de-activating the skin sensor to cover the needle and locking the skin sensor in the de-activated position. The method may further comprise reloading the auto injector by operation of the reload handle, wherein the reloading may comprise moving the syringe assembly from the second position to the first position, reloading the syringe driver, locking the syringe assembly in the first position and unlocking the skin sensor whereby the auto injector is ready for delivering a further dose of medicament.

In some embodiments of the present invention, an auto injector for delivering at least one dose of medicament is provided. The auto injector may have a housing for accommodation of a syringe assembly comprising a syringe with a needle. The syringe assembly may be movably positioned in the housing between a first position in which position the needle is accommodated inside the housing and a second position in which position the needle protrudes outside the housing. The auto injector may further comprise a sound generator configured to emit a sound while dosing.

Throughout the present disclosure, the auto injector has a front or forward end in the end intended to be pushed against a patient's skin, and a back or backward end towards the other end of the auto injector. The terms "forward" or "downward", such as forward or downward movement therefore means towards the forward end, or towards the skin of a patient when the auto injector is positioned in its intended operational position for injection. Likewise, backwards or upwards, such as backwards or upwards movement, means towards the back end of the auto injector, or away from the skin of a patient when the auto injector is positioned in its intended operational position for injection. Furthermore, a top end of the auto injector is the back ward end of the auto injector, i.e. the end furthest away from the skin of a patient when the auto injector is positioned in its intended operational position for injection.

Furthermore, the term "reload" means to ready the auto injector for a further injection using the same or a different syringe. The reloading of the auto injector is performed while the syringe is provided in the auto injector. When a driver, such as a spring, is reloaded or re-activated, power is transferred back to the driver. For example, the reloading or re-activation of a spring comprises the reloading of tension on the spring.

In one or more embodiments of the present invention, the reloadable auto injector may be activated upon unpacking of the device. Especially for emergency injections of medicament, it is advantageous for an operator or patient that no further steps are necessary after unpacking the device and before activation of the auto injector, such as by pushing the skin sensor against the skin of a patient.

In one or more embodiments of the present invention, the syringe driver and the plunger rod driver are separate drivers. Thus, the syringe driver may separate from the plunger rod driver, and in some embodiments, the syringe driver may be a resilient device, such as a spring, such as a compression spring. Likewise, the plunger rod driver may be a resilient device, such as a spring, such as a compression spring. The syringe driver may be configured to act on the syringe assembly, to drive the syringe assembly from the first position to the second position. The syringe driver may be provided in the housing and the housing may guide or stabilized the syringe driver. The plunger rod driver may be configured to act on the plunger rod and may be provided within a plunger rod tube. The plunger rod tube may guide or stabilize the plunger rod driver.

The auto injector may in some embodiments further comprise a syringe lock configured to lock the syringe in the first position, and a skin sensor configured to release the syringe lock upon engagement with the skin of a patient wherein the skin sensor is activated by pressing the skin sensor onto a patient's skin.

The skin sensor may thus be of a cylindrical shape encompassing at least a part of the syringe assembly, and the skin sensor may be configured to connect to a skin sensor driver. The skin sensor driver may be a resilient driver, such as a spring. In one or more embodiments, the skin sensor driver is a spring, and the spring may be configured to be in the relaxed position when the skin sensor is positioned in a forward position. The skin sensor may for example be activated upon pressing the skin sensor against the skin of a patient. Hereby, the operator may compress the skin sensor driver, such as the spring, and move the skin sensor backwards away from the skin. The compressed skin sensor driver, such as the spring, may be released as soon as the auto injector is removed from the skin and the skin sensor will thereby be pushed forward by the skin sensor driver.

In one or more embodiments, the auto injector may further comprise safety features, such as a needle protection element, such as a needle shield, to shield the needle and prevent accidental contact with the needle. In some embodiments, the skin sensor may shield the needle and thus act as a skin sensor configured to release the syringe driver as mentioned above, and further act as needle protection element configured to shield the needle. It is however envisaged that the needle protection element, such as the needle shield, may be an element separate from the skin sensor. In the following, reference may be made to the skin sensor, however, it will be clear for a person skilled in the art that corresponding needle protection features could be evenly applied to a needle protection element separate from the skin sensor.

The needle protection element, such as the skin sensor, may be able to lock in a forward position so as to prevent accidental contact with the needle. The needle protection element may for example be locked after a dose has been injected, and in between multiple injections. The needle protection element may for example comprise a locking protrusion and the locking protrusion may be configured to rest on a ledge in the syringe lock when a first dose has been delivered locking the needle protection element in the forward position and preventing backward motion of the needle protection element. It is envisaged that the locking of the needle protection element also may be implemented using any other locking mechanism.

The skin sensor may likewise have a locked forward position and an unlocked forward position, and the skin sensor may for example be locked after each injection cycle has been completed. It is an advantage of locking the skin sensor after an injection cycle has been completed in that the risk of accidental activation of the auto injector for a further injection is minimized or eliminated. By locking the skin sensor in the locked forward position, it requires a clear operator or patient input to re-activate the auto injector and prepare it for a further injection cycle. The skin sensor may for example comprise a locking protrusion and the locking protrusion may be configured to rest on a ledge in the syringe lock when a first dose has been delivered locking the skin sensor in the forward position and preventing backward motion of the skin sensor. It is envisaged that the locking of the skin sensor may be implemented using any other locking mechanism.

The reloading handle may be configured to further interact with the needle protection element and/or the skin sensor to unlock the needle protection element and/or the skin sensor upon reloading, and in one or more embodiments, rotation of the reload handle rotates the syringe lock to thereby unlock the needle protection element and/or the skin sensor. In the unlocked position, backward motion of the needle protection element and/or the skin sensor may be enabled to thereby ready the auto injector for a further injection. In one or more embodiments, the needle protection element and/or the skin sensor is in an unlocked position upon unpacking of the device and locked after a dose of medicament has been delivered.

It is an advantage of providing the auto injector in a ready-to-use state right out of the package in that the auto injector may be applied for emergency injections of medicament, such as by an anaphylaxis allergy reaction, etc. Thus, for a patient or user, it is of utmost importance that no considerations or user manual as to the functioning of the auto injector is required, but that the device may inject the medicine directly be pushing the auto injector against the skin.

It is an advantage of providing a locking of the needle protection element and/or the skin sensor after the delivery of a dose in that the auto injector in this state may either be discarded or await a further injection of medicament. In both instances it is advantageous that there is limited or no risk of neither a patient, a user nor any one handling the discarded auto injector to contact the needle and/or to accidentally activate the auto injector to perform a further dose injection cycle.

Using the reload mechanism to further unlock safety features, such as the needle protection element, the skin sensor, etc., provides the advantage of having an auto injector with safety features which is fully reversible upon reloading of the device. Thereby an auto injector may be provided with the safety features of a standard auto injector provided in a fully reversible reloadable auto injector.

The syringe may be locked in the first position when the auto injector is in a position ready for delivering a dose. The syringe may thus be locked in the first position initially, i.e. when the auto injector is unpacked, and after each reload action. The syringe may be locked in the first position by a syringe lock. The syringe lock may for example be released upon activation of the skin sensor.

The activation of the skin sensor may be configured to cause a backward movement of the skin sensor whereby a skin sensor angled surface may be configured to engage with a syringe lock angled surface translating the lateral motion of the skin sensor into angular motion of the syringe lock. The skin sensor may for example be activated by pressing the skin sensor against the skin of a patient to thereby force the skin sensor backwards. The syringe lock may have a cylindrical shape and may be configured so that the skin sensor, upon moving backward, slides inside the syringe lock. The skin sensor angled surface may thus be a protrusion on an outer side of the skin sensor, and the syringe lock angled surface may be a protrusion on a syringe lock inner side, so that when the skin sensor slides inside the syringe lock the skin sensor angled surface and the syringe lock angled surface may engage so that the skin sensor angled surface thereby forces the syringe lock to rotate.

The syringe lock may further comprise a resting ledge, and the syringe assembly may rest on the resting ledge in the syringe lock to thereby lock the syringe assembly in the first position. The angular motion of the syringe lock may release the syringe assembly by turning the syringe lock and thereby free the syringe assembly from the resting ledge.

In one or more embodiments, the syringe lock may further comprise a syringe lock guide slot, and the syringe assembly may comprise a syringe assembly tap; the syringe assembly tap may be configured to move in the syringe lock guide slot. The syringe lock guide slot may comprise the resting ledge, and the rotation of the syringe lock may move the tap in the guide slot from the resting ledge to a released position in which the syringe assembly tap may follow a downward guide slot path from the released position adjacent the ledge to a syringe lock end stop thereby moving the syringe assembly from the first position to the second position. Thus, the syringe assembly may be moved from the first position to the second position when the syringe assembly end stop travels in the syringe lock guide slot from the released position to the syringe lock end stop.

At least a part of the guide slot may comprise an inclined guide slot so that the syringe lock may be further rotated upon the movement of the syringe assembly from the first position to the second position.

The syringe assembly may thus be locked in the first position where forward movement is restricted by the syringe lock, such as by the resting ledge. As the syringe lock is rotated, the syringe assembly may be free to move forward and the syringe driver may thereby be released to move the syringe assembly from the first position to the second position. The forward motion may thus be restricted by the syringe assembly tap engaging a syringe lock end stop. A distance along the longitudinal axis of the auto injector from the resting ledge to the end stop may thus indicate the travel of the needle from the first position to the second position and thereby, the end stop may define the insertion depth for the needle.

It is seen that the syringe lock may control the movement, such as the forward movement, and for example the movement from the first position to the second position, of the syringe and/or the syringe assembly. Thus, the syringe lock may control the needle insertion.

The syringe assembly may comprise a syringe tube co-axially encompassing the syringe and a plunger rod tube co-axially encompassing the plunger rod, the syringe tube and the plunger rod tube being interconnected via syringe tube connectors engageable with plunger rod connectors.

The plunger rod driver may in one end be fixedly connected to a back end of the plunger rod tube and in another end be configured to engage the plunger rod. The plunger rod driver may be locked while the syringe assembly is moved from the first position to the second position, and thus, the plunger rod may be kept in the same position while the syringe assembly is moved from the first position to the second position. Thus, the plunger rod driver, the plunger rod and the plunger rod tube may be moved forward by the syringe driver.

The plunger rod may be configured to be released when the syringe assembly is in the second position thereby activating the plunger rod driver to move the plunger rod forward. Hereby, the plunger rod may engage the syringe stopper and thereby forcing the syringe stopper forward and deliver a dose of medicament. The plunger rod may typically move forward a predetermined distance in the syringe before a plunger rod stop engages the plunger rod and prevents further forward movement of the plunger rod. The predetermined distance may indicate the amount of medicament delivered, depending on syringe size.

The plunger rod driver may be configured to move the plunger rod a first predetermined distance upon a first activation of the plunger rod driver, a second predetermined distance upon a second activation of the plunger rod driver, a further predetermined distance upon a further activation of the plunger rod driver, etc., before engaging a first plunger rod stop, a second plunger rod stop and/or any further plunger rod stops. The first, the second and/or further predetermined distances may be different distances to allow for different doses of medicament to be delivered following first, second and/or further activations of the auto injector.

The second or further activation of the plunger rod driver may follow a reload of the auto injector, and thus follow any movement of the syringe assembly from the first position to the second position. The movement of the syringe assembly from the first position to the second position may thus comprise moving the plunger rod, the plunger rod driver and the plunger rod tube with the syringe assembly. Thereby, the plunger rod may remain locked upon any plunger rod stop, and the plunger rod driver may not be able to drive the plunger rod forward while moving the syringe assembly from the second position to the first position. The plunger rod may, after a first injection cycle has been completed, not be released until the syringe assembly, following activation of the auto injector, is moved from the first position to the second position a second and/or further time.

In one or more embodiments of the present invention, an auto injector having sequential control of needle insertion and dose injection is provided. The auto injector may have a housing for accommodation of a syringe with a needle, and the syringe may be movably positioned in the housing between a first position in which position the needle is accommodated inside the housing and a second position in which position the needle protrudes outside the housing. The housing may furthermore accommodate a plunger rod configured to be advanced in the syringe for delivering at least one dose of medicament, and a plunger rod tube. The plunger rod tube may have at least one locking member configured to interact with a plunger rod stop to normally lock the plunger rod to the plunger rod tube. A syringe driver may be configured to apply a force to the syringe thereby moving the syringe from the first position to the second position and the syringe driver may further be configured to advance the plunger rod tube with the plunger rod to the second position. A plunger rod driver may be configured to apply a force to the plunger rod to advance the plunger rod in the syringe for delivering at least one dose of medicament. The housing may be configured to unlock the locking member and release the plunger rod from the plunger rod tube when the syringe and the plunger rod tube is advanced to the second position. Thereby the plunger rod driver may be activated to advance the plunger rod in the syringe for delivering of at least one dose of medicament. Thus, the syringe driver and the plunger rod driver may be separate drivers.

According to one or more other embodiments of the present invention, an auto injector having sequential control of needle insertion and dose injection is provided. The auto injector may have a housing for accommodation of a syringe with a needle, and the syringe may be movably positioned in the housing between a first position in which position the needle is accommodated inside the housing and a second position in which position the needle protrudes outside the housing. The housing may furthermore accommodate a plunger rod configured to be advanced in the syringe for delivering at least one dose of medicament, and a plunger rod tube. The plunger rod tube may have at least one locking member configured to interact with a plunger rod stop to normally lock the plunger rod to the plunger rod tube. A first spring may be configured to apply a force to the syringe thereby moving the syringe from the first position to the second position and the first spring may further be configured to advance the plunger rod tube with the plunger rod to the second position. A second spring may be configured to apply a force to the plunger rod to advance the plunger rod in the syringe for delivering at least one dose of medicament. The housing may be configured to unlock the locking member and release the plunger rod from the plunger rod tube when the syringe and the plunger rod tube is advanced to the second position. Thereby the second spring may be activated to advance the plunger rod in the syringe for delivering of at least one dose of medicament.

It is a further advantage of providing a first spring configured to advance the syringe in the housing and a second spring configured to advance the plunger rod in the syringe that the spring characteristics may be selected according to the purpose. For example, to drive a needle into the skin a significantly smaller force may typically be needed than when injecting a medicament from a syringe, depending on needle bore. Thus, especially, when the initial force is lower than the force needed for the injection of the medicament, the design of the springs may be complex, and difficult obtainable by a single spring.

In particular when injecting a medicament into muscle tissue, a longer needle is typically used compared to needles used for subcutaneous injections. In consequence of the long needle size and still the requirement of a minimum force to facilitate injection of the medicament into the muscle tissue, a significant force may have to be stored in the spring. A high potential energy stored in the spring during the entire shelf life of the auto injector, also adds to the requirements for the surrounding parts of the auto injector in particular relating to strength and hence cost of manufacturing.

Furthermore, when manufacturing the auto injectors in high volume, the small tolerances required when using a single spring for both needle insertion and medicament injection may be critical. Thus, it is a further advantage of the present invention that as few parts as possible move in relation to each other to thereby obtain a system which is more robust with respect to the manufacturing process. Also, providing one spring to both insert a needle and inject a medicament requires for the spring to be able to extend over a significant length compared to the spring diameters which may typically be provided for in auto injectors. Furthermore, the design of the spring characteristics, such as force distribution, may be much simpler, and therefore reduce the costs of the springs.

It is seen that the locking member cooperating with the housing or an intermediate member, such as the reload handle, may control the movement of the plunger rod. Thus, the movement of the plunger rod and thereby the injection of medicament is controlled by the housing or the intermediate member.

It is a further advantage of the present invention, that the means for releasing the syringe to allow insertion of the needle are decoupled from the means for releasing the plunger rod for injection of medicament. Thus, there is no direct coupling between the end stop for the needle insertion, which is provided on the syringe lock, and the release of the plunger rod, which is provided by alignment of plunger rod tube and housing or the intermediate member, such as the reload handle. Thereby, an inaccuracy in the needle injection procedure will not inherently be transferred to the injection of medicament. Thus, while the release of the syringe may be configured to release the plunger rod, the release of the syringe may be mechanically decoupled from the plunger rod release.

The locking member may comprise at least one deflectable member and the housing may be configured to allow for the at least one deflectable member to enable deflection away from the plunger rod when the syringe and the plunger rod tube has been advanced to the second position.

In one or more embodiments, the plunger rod tube and the syringe may be interconnected so that the plunger rod tube may not be able to move with respect to the syringe and vice versa.

The housing may have an opening, such as a window or a widened portion, configured to be aligned with the at least one deflectable member when the plunger rod tube is advanced to the second position. By aligning the at least one deflectable member with the opening, the at least one deflectable member may be configured to deflect through or towards the opening. When the plunger rod tube with the at least one deflectable member is not in the second position, an inner surface of the housing may prevent the at least one deflectable locking member from deflecting, such as from deflecting outwards, i.e. deflecting radially with respect to a longitudinal axis of the syringe and/or the plunger rod tube. Hereby, the plunger rod may be locked to the plunger rod tube and the plunger rod driver, such as the second spring, will remain in a compressed state and not be able to force the plunger rod forwards in the syringe. Only when the plunger rod tube is aligned with the housing openings will the at least one deflectable member be able to deflect and thereby release or unlock the plunger rod from the plunger rod tube. As the plunger rod is released from the plunger rod tube, the plunger rod driver will be activated and force the plunger rod to advance in the syringe to thereby deliver a dose of medicament.

Thus, upon release of the plunger rod, the plunger rod driver may advance the plunger rod within the syringe in that the plunger rod stop is able to pass the deflected locking member. Thereby, the forward end of the plunger rod is advanced in the syringe, and the plunger rod stop may move forward to an end-of-dose stop in the plunger rod tube. Thereby, the dose to be injected may be determined by the distance from the release of the plunger rod, to the end-of-dose stop times a diameter of the syringe.

The plunger rod stop may have an angled surface normally pressing against an angular surface of the deflectable locking member. Hereby, the plunger rod forces the deflectable locking member to deflect towards the opening when the plunger rod is being pushed forward by the plunger rod driver In one or mere embodiments, the at least one deflectable locking member may be hinged to the plunger rod tube in a downward position with respect to the movement of the plunger rod. Hereby, the at least one deflectable locking member is stronger in that push forces, and not pull forces, are exerted on the at least one deflectable locking member. Another advantage of hinging the deflectable locking member in a downward position is that it is ensured that the deflectable locking member may deflect only when the entire length of the deflectable locking member opposes the full opening. This further implies that the auto injector is more robust in the control of ensuring strict sequential execution of medicament injection only after a fully established needle insertion. In particular, for acute medications with very fast injection of a drug, i.e. when a large bore needle is used, it is of outmost importance that the sequential control is robust.

As mentioned above, the plunger rod driver may comprise a spring, such as a compression spring, and in some embodiments, the plunger rod spring may in one end be fixedly connected to the plunger rod tube.

The plunger rod driver may apply the driving force directly onto the plunger rod, such as onto a plunger rod flange, so as to for example drive only the plunger rod forwards. It is an advantage of applying the driving force directly onto the plunger rod in that no complex parts may be necessary to shift the loading between different parts, and furthermore, the force may be applied in a controlled manner, with substantially no or significantly reduced uncertainty as to how much force will actually be applied to the plunger rod, and thereby, how fast the medicament will be expelled.

The plunger rod driver, such as the second spring, may for example be provided inside the plunger rod tube, and the syringe driver, such as the first spring, may be provided outside the plunger rod tube.

The housing may further accommodate a syringe tube for holding the syringe, and the syringe may have a syringe flange which may then be locked between the syringe tube and the plunger rod tube. Hereby, a syringe assembly comprising the syringe, the syringe tube interconnected to the plunger rod tube in which the plunger rod and the plunger rod driver are positioned, may be moved as one entity. It is an advantage of locking the syringe, the syringe tube and the plunger rod tube together in that no accidental movement of the parts in relation to each may influence the delivery of the medicament.

In one or more embodiments, the auto injector may be a reloadable auto injector.

In some embodiments, the auto injector may be configured to deliver more than one dose of medicament, such as two doses of medicament, such as a plurality of doses of medicament, etc., such as two separate doses of medicament, etc. In some embodiments, the delivery of a second or any further doses may require a clear operator input to activate the auto injector for the further injection. The plunger rod tube may comprise at least a first and a second locking member to enable delivering of a first and/or a second dose, or the plunger rod tube may comprise a plurality of locking members to enable delivery of a first, second and/or plurality of doses. Each of the first, second and/or plurality of locking members may be configured to consecutively engage with the plunger rod stop. The first, second and/or plurality of locking members may be a first, second and/or plurality of deflectable locking members. It is an advantage of the present invention that the two windows for release of the plunger rod tube are provided on a same component, i.e. on the reload handle, in that manufacturing tolerances are better controllable.

The housing may comprise a first, a second and/or a plurality of openings configured to align with the first, second and/or plurality of locking members, respectively, when the syringe is the second position.

It is envisaged that the opening(s) may be provided in any intermediate element, such as in a handle, positioned between the housing and the plunger rod tube. Thus, the deflectable locking members may be restricted by an inner side of such an intermediate element and the opening(s) may be provided in the intermediate element only or in any intermediate element and the housing, to e.g. allow for a full deflection of the locking members.

It is envisaged that the principle as set out allow for any number of injections, and the auto injector may comprise one, two and/or a plurality sets of locking members and corresponding openings wherein each locking member and corresponding opening may be provided at independent positions on the perimeter of the housing and/or any intermediate element and the plunger rod tuber, respectively.

It is an advantage of providing the openings in one element, such as in the housing or in an intermediate element, in that substantially only the tolerances in the manufacturing of the one element influences the dose delivery control. Thereby, the first and any further doses delivered may be aligned with each other, and thereby highly controllable.

To deliver more than one dose, the auto injector may be activated more than once, thus, also the plunger rod driver may be activated one or more times. The plunger rod driver may be configured to move the plunger rod a first distance upon a first activation of the plunger rod driver and a further distance upon a further activation of the plunger rod driver.

The plunger rod stop may engage the second or further locking member after a first or further medicament injection has been performed. Thus, for example, when a first dose has been delivered, the plunger rod stop will engage the second deflectable locking member, and thereby be ready for delivering of a second dose as soon as the second deflectable locking member is aligned with the second opening in the housing.

In one or more embodiments, the second activation of the plunger rod driver may follow a reload of the auto injector, and a repeated movement of the syringe and/or the syringe assembly from the first position to the second position.

In one or more embodiments, the user operation of the reload handle, so as to for example activate the auto injector and thereby ready the auto injector for a second and/or further delivery of medicament, may comprise a rotational movement.

The reload handle may be configured for a rotational movement, and the auto injector may further comprise an intermediate component, such as a torsion ring, transferring the rotational movement of the reload handle to a translational movement of at least the syringe assembly.

The intermediate component which may be interconnected to the syringe assembly may have a tap configured to move longitudinally along a guide or surface of the reload handle to thereby retract the syringe assembly from the second position to the first position upon user operation of the reload handle. The guide or surface of the reload handle may in some embodiments be an inclined guide or surface of the reload handle, and the tap may move along the inclined surface upon operation of the reload handle. Thereby, the syringe assembly may be forced along the inclined surface to move the syringe assembly from the second position to the first position, and may further rotate the syringe assembly. Hereby, the syringe assembly may follow the guide in the syringe lock into the first position.

A complete operation of the reload handle may force the tap on the intermediate component over an inclined surface top and into a second or further reload handle slot. Thus, after the retraction of the syringe assembly, the syringe assembly is further rotated. This rotational movement may allow for the syringe assembly to be rotated onto the syringe lock ledge and lock the syringe assembly in the first position and thereby ready the device for a further delivery. Thus, when the intermediate component tap reaches the second or further reload handle slot, the syringe assembly is rotated onto the syringe lock ledge.

The second and/or any further reload handle slots may have an inclined surface to allow for continuous reloading of the auto injector. In one or more embodiments, the reload handle comprises two inclined reload handle slots to allow for continuous reloading of the auto injector.

The second reload handle slot may be a slot substantially parallel with a longitudinal axis of the auto injector, with no inclined surface tops, thus, the second and/or further reload handle slot may allow for longitudinal movement only to thereby prevent further reload of the auto injector. Thus, the reload handle may not be able to reload the auto injector and ready it for a further injection as the intermediate component will not be able to translate the rotational movement of the handle to translational movement of the syringe assembly.

The reload operation may be configured to reverse the operation of the auto injector and may for example reverse syringe driver, syringe lock, skin sensor, etc.

In one or more embodiments, the auto injector housing may further comprise an indication of a "ready" state and a "not ready" or "done" state. The "ready" state may indicate a first rotational position of the syringe lock in which position the syringe assembly is locked in the first position. As the syringe assembly may be rotated upon injection with respect to the housing, and further moved forward with respect to the housing, the "ready" state may not be shown in the window unless the syringe assembly is in the first locked position. The "ready" state may furthermore only be indicated to an operator or patient when the skin sensor is in the unlocked state. Thus, the "ready" state may indicate that the auto injector is ready to use when unpacked, and indicate that the auto injector is ready to use after reloading of the auto injector.

The indication may be provided as a label window which may reveal information provided in for example the syringe lock or any other structural element beneath the housing in which a "ready" state is indicated, either by inscription, by color coding, etc. The indication may also be provided be an inspection window which may be a window provided so that the drug or medicine in the syringe is visible when the auto injector is in the ready state, and wherein the view of the drug or medicine is obscured when the auto injector is in any "not ready" or "done" state.

The inspection window may further provide a view of the medicine before the auto injector is used for injection of medicine to thereby provide a visible check of medicine availability, medicine color, quality, etc.

The skin sensor and/or needle shield may extend over the length of the needle when the syringe assembly is in the first position to hide the needle from a patient's or user's view and the skin sensor and/or needle shield may further be configured to extend over the length of the needle as the needle is withdrawn after a dose has been delivered.

In one or more embodiments, the auto injector may be configured to provide a sound while delivering a medicament, so that a sound is generated while dosing by e.g. a sound generator. The sound may be generated during the entire delivery of a dose, or the sound may be generated during at least a part of the delivery of the dose, such as during more than 50% of the time of delivery, during the last third of the time of delivery, during substantially the entire time of delivery, etc. Thus, the auto injector may further comprise a sound generator configured to emit a sound while dosing, and in some embodiments, the sound generator may comprise a ratchet mechanism. The ratchet mechanism may be any conventional ratchet mechanism, such as a ratchet mechanism comprising flexible arms positioned with the syringe assembly for engaging sloped teethes on the plunger rod, for example such as to allow for forward movement only of the plunger rod.

Typically, when delivering a medicament with an injector, it is advantageous to keep the needle in place under the skin for a period of time after the injection has taken place. Hereby, the uptake of the medicament may be improved significantly, and furthermore, the risk of the medicament leaking out of the injection site may be reduced. However, for a patient or a user, it may be difficult to tell when the injection has been completed and thus from when the period of time after injection should be determined.

In some prior art embodiments, a sound has been generated after the dose has been injected, i.e. after the injection cycle has been completed, however, for a patient or a user, this means that there are three phases during the injection; first a silent phase while the medicament is injected, than a sound phase, i.e. the end-of-dose signal, and then again a silent phase in which the patient or user has to keep the needle under the skin. For a patient or user, especially a user under stress, which may be the case if it is an emergency injection of medicament, this may be difficult to administer.

It is therefore an advantage of generating a sound during at least a part of the delivery of the dose, to thereby indicate with a sound when medicament is injected, that is, the sound is provided while dosing, and when the sound stops, the user may have to keep the needle under the skin for a period of time. This results in only two phases, an injection phase with sound, and a silent phase in which the user may have to keep the needle under the skin and this procedure may be simpler to administer for a user.

To generate the sound while dosing, a sound generator or noise maker, such as a ratchet mechanism, may be integrated with the auto injector.

For example, the plunger rod may be a linear ratchet having a number of teeth configured to interact with a number of pawls provided in connection with the plunger rod tube, so as to generate a sound while the plunger rod is extended passed the pawls. The ratchet mechanism may comprise flexible arms positioned with the syringe assembly for engaging sloped teeth on the plunger rod.

A ratchet mechanism inherently allow movement in one direction only, thus providing a ratchet mechanism with the plunger rod allow for movement in a forward direction only, and may prevent the plunger rod from being returned to its initial position. Thus, the sound generator may further act as an anti-tampering component, in that the ratchet mechanism ensures that a used auto injector may not be separated and be retro-fitted with another syringe for a new patient or user as the plunger rod cannot be retracted from the syringe into the initial position.

In one or more embodiments, the syringe assembly may further comprise an anti-tamper component, such as a tamper protection, and the anti-tamper component may for example comprise protection mechanism to ensure that backward movement of the plunger rod is prevented, such as a ratchet mechanism, such as a ratchet mechanism allowing for forward motion of the plunger rod only.

In one or more embodiments, the auto injector may be re-usable, thus, a user may be able to disassemble the auto injector to replace the syringe. For example, a user may be able to replace the syringe with needle only, or a user may be able to replace the syringe assembly with a new syringe assembly.

Typically, the auto injector may be provided in a casing and the casing may have to be removed before the auto injector is ready to be used.

A medicinal cartridge or pre-filled syringe is typically provided with a needle. To protect the needle during transportation and to enable sharps protection, the syringe needle is typically provided with a soft protective part and a rigid protective part, i.e. the rigid needle shield, RNS. To ready the auto injector for injection, typically, both the soft protective part and the rigid protective part needs to be removed. However, both for safety reasons, and because the protective parts may be difficult to access for a user, a rigid needle shield removal part may be implemented. The rigid needle shield removal part may at least partly enclose the rigid protective part and for example grip a ridge on the rigid protective part so that the rigid protective part may be removed with the removal of the rigid needle shield removal part.

The casing, such as a transportation housing, may be removed by for example a straight pulling motion, a twist, a combination of these, or in any other way as known by a person skilled in the art. In some embodiments the casing may surround the syringe assembly, but not the reload handle. The casing may be held in place by a ring snap mechanism provided between the reload handle and the casing. The casing and the reload handle assembly may be sealed by a piece of adhesive tape wrapped around the casing and the reload handle assembly. The casing may be removed from the auto injector by twisting the casing slightly against the reload handle, utilizing for example a tapered knob on the auto injector to translate the rotational force into a longitudinally movement which breaks, partly by the rotation and partly by the axial displacement in the longitudinal direction, the ring snap mechanism. Also due to the longitudinal displacement the RNS removal part may start to pull off the RNS where the remaining dismantling of the RNS is carried out by the operator. The gearing by the rotation over the tapered knob helps the operator to more easily overcome potential high stick-forces for the RNS after longer time of storage, once moved a small distance the operator may easily pull off the RNS the remaining distance at much less force input. The twisting of the reload handle relative to the casing may generate a longitudinal movement in any know way, e.g. by a tapered knob to translate the rotational force into a longitudinal movement, or by an internal thread where unscrewing in one predetermined rotational direction would yield longitudinally separation between the handle and casing, etc.

The RNS (Rigid Needle Shield) may cover the injection needle on the syringe and may be pre-mounted on the syringe before assembling the auto injector. The step of readying an auto injector for injection, may comprise the step of removing the rigid needle shield whereby the injection needle becomes exposed. In some embodiments, the removal of the RNS may be an integrated part of the auto injector device activation process and hence automated in view of the operator, user or patient. The RNS removal part may be provided so that the auto injector including the RNS is not tampered with during storage, and furthermore, the RNS may be protected so that any significant physical dislocation from its initial sealing position of the RNS is avoided. Such physical dislocation may be e.g. be a radial or a longitudinal displacement or caused by rocking motions etc. and such physical dislocation may have a serious impact on auto injector performance. The process of removing the RNS may be robust and reliable but at the same time, the seal provided by the RNS should be efficient. Thus, the automated removal of the RNS upon device activation may ensure none or minimal physical interaction from outside forces to the RNS during the storage period.

Still, upon device activation the RNS removal may be highly robust as otherwise it may potentially be difficult for the operator to gain access for manual removal. Thus, the mechanism interfacing to the RNS may have to satisfy two opposite requirements. Furthermore, the assembly of the auto injector with the RNS removal part may be easy and intuitive.

In some embodiments, the RNS removal part may have a general cylindrical shape but may have slits along its side to allow for insertion of the entire RNS. Furthermore, the RNS removal part may have a U-shaped cut-out on the end surface towards the syringe in order to allow the presence of the syringe, and the diameter/size of the U-shaped cut-out may be designed to be smaller than the maximum diameter of the RNS but large enough to not be in physical contact during storage, i.e. not touch upon syringe or upper portion of the RNS. With the RNS removal part in place, a longitudinal force pulling away from the syringe will now ensure engagement between RNS removal part and the larger diameter rime on the RNS and may thereby force the RNS to be pulled off of the syringe.

The RNS removal part may be applied sideways to the RNS and syringe assembly, or the RNS removal part may be applied longitudinally, thereby pushed onto the RNS and syringe assembly from the front. A number of extended hooks may grip behind the RNS to facilitate pulling off of the RNS by exertion of pull forces on the RNS removal part. In another embodiment, a number of deflectable extended fingers with hooks to reach behind the RNS may be envisioned both allowing for sideways assembly or longitudinal or axial assembly.

In one or more embodiments, the RNS removal part may furthermore cooperate with the skin sensor so that e.g. deflectable parts, such as deflectable finger hooks, may be forced inside the skin sensor during removal through a tight diameter fit. For example, the skin sensor may have an internal diameter, such as 12 mm, to just allow the hooks to pass through but any potential radial deflection of the hooks, i.e. when subjected to the stress exerted from the pulling force, may be minimized due to marginal available space between the deflectable parts outer radial extension (diameter) and the inner diameter of the skin sensor.

The present invention will now be described more fully hereinafter with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout. Like elements will, thus, not be described in detail with respect to the description of each figure.

BRIEF DESCRIPTION OF THE DRAWINGS

FIGS. 4A-C show an auto injector handle top and corresponding casing, FIGS. 5A-E show a rigid needle shield remover component.

DETAILED DESCRIPTION OF THE DRAWING

Figure 1:
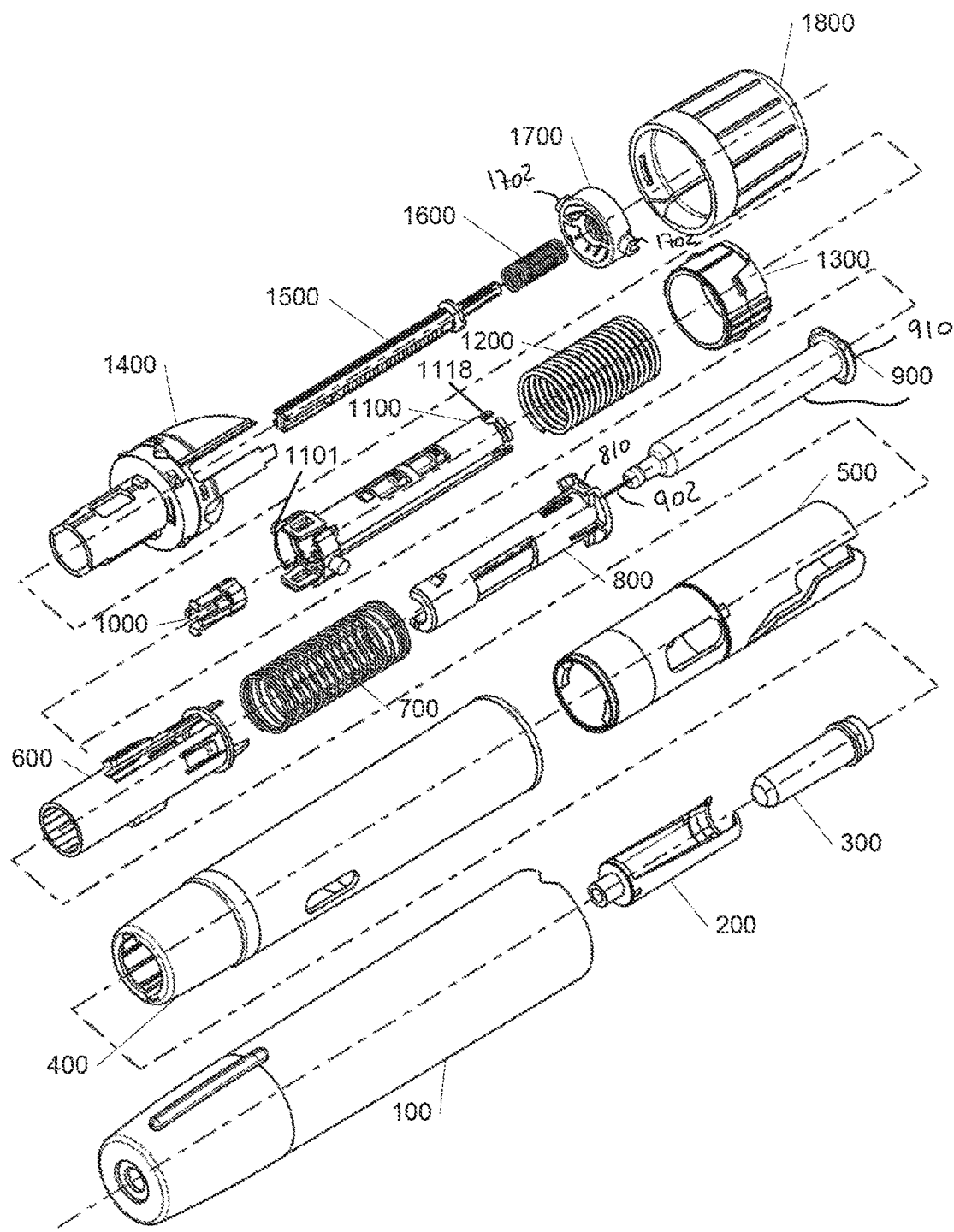
FIG. 1 shows an exploded view of an auto injector.
Figure 2A:
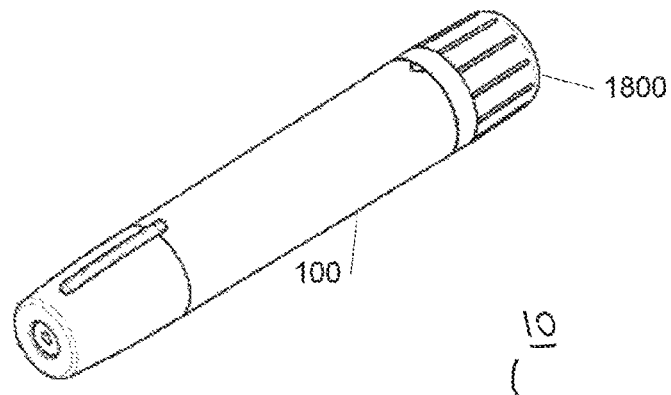
FIGS. 2A-G show exemplary a view of the auto injector in various states as seen from a user perspective.
Figure 2B:
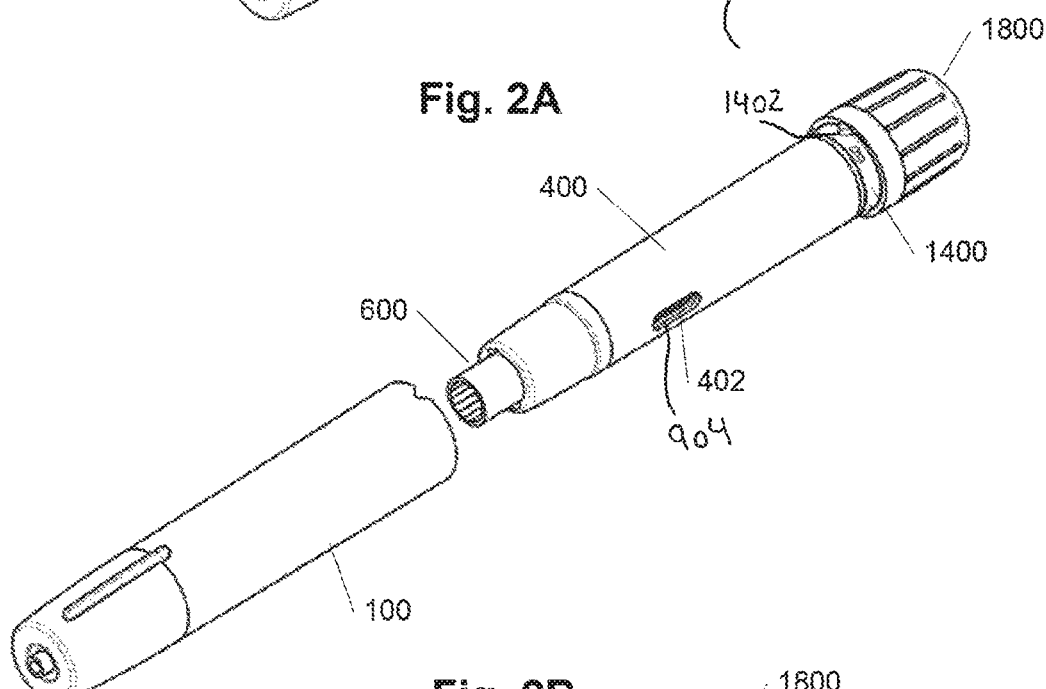
Figure 2C:
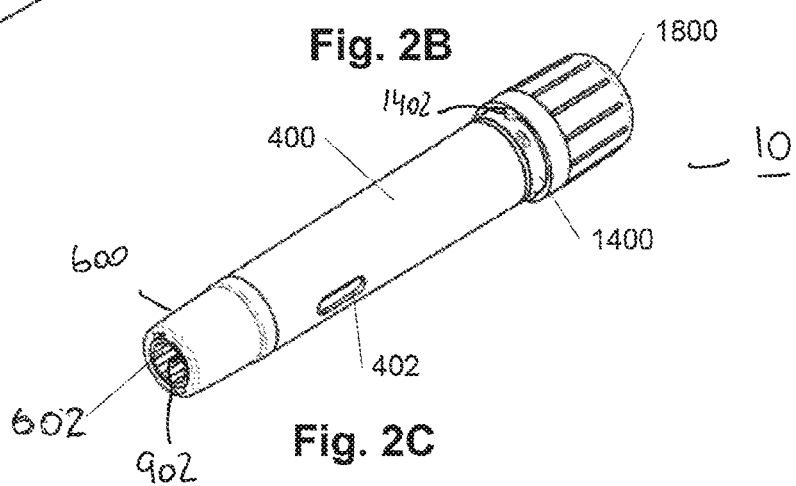
Figure 2D:
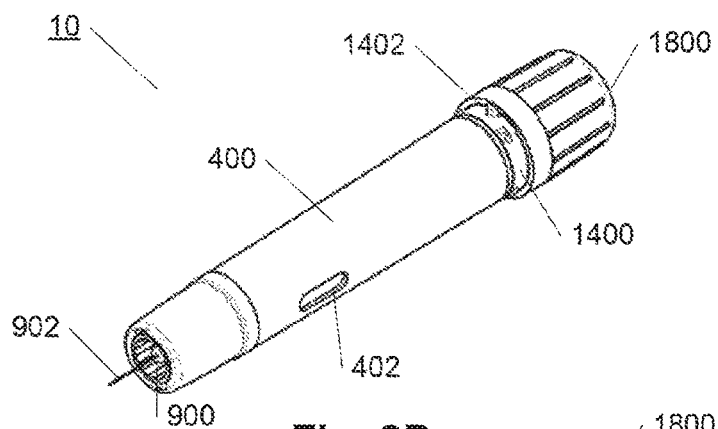
Figure 2E:
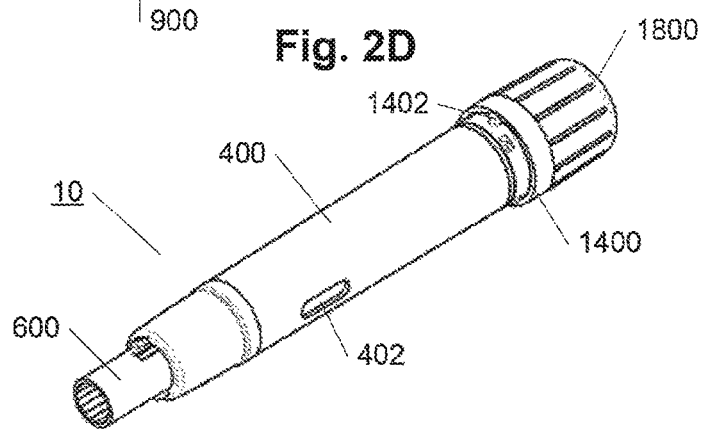
Figure 2F:
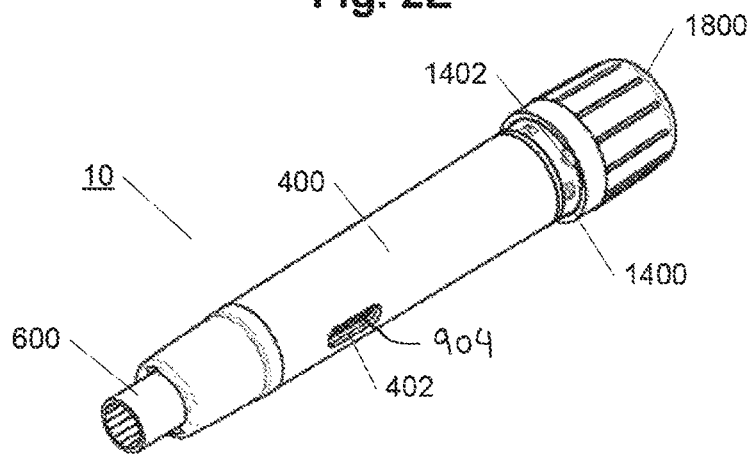
Figure 2G:
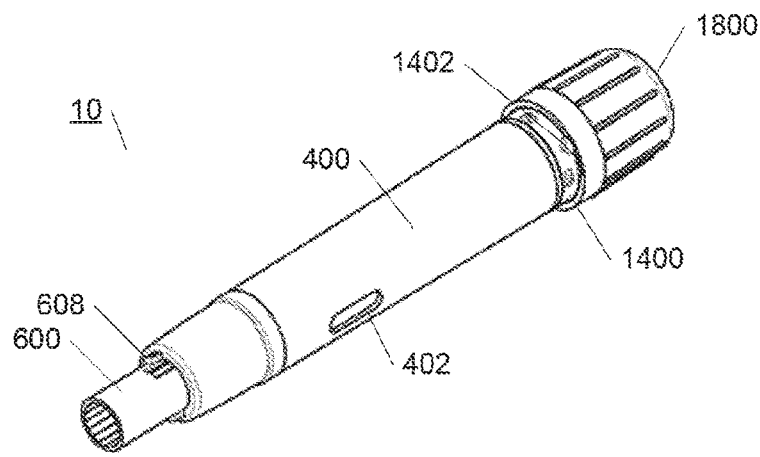

In the following an auto injector according to any of the above described aspects of the invention will be described in more detail and with reference to the drawings. A reloadable auto-injector 10 with a housing 400 for accommodation of a syringe assembly 20 is provided. The syringe assembly 20 may comprise a syringe 900 with a needle 902, and the syringe assembly 20 may be movably positioned in the housing 400 between a first position in which position the needle 902 is accommodated inside the housing 400 and a second position in which position the needle 902 protrudes outside the housing 400. The syringe assembly 20 may further comprise a syringe stopper 908 movably positioned in the syringe 900 and sealing syringe content 904, a plunger rod 1500 configured to engage the syringe stopper 908, and a plunger rod driver 1600 being configured to apply a force to the plunger rod 1500 to advance the plunger rod 1500 in the syringe 900 for delivering at least one dose of medicament. Furthermore, a syringe driver 1200 may be accommodated inside the housing 400 and be configured to apply a force to the syringe assembly thereby moving the syringe 900 from the first position to the second position. The housing 400 may still further comprise a reload handle 1400 configured to reload the auto injector 10 for injecting a further dose of medicament, wherein the reload handle 1400 may be connected to the syringe assembly so that user operation of the reload handle 1400 is configured to retract the syringe assembly to the first position and to simultaneously reload the syringe driver 1200 to thereby ready the auto injector for delivering a further dose of medicament.

In FIG. 1 an exploded view of a syringe driver according to an embodiment of the present invention is provided. A casing 100 is provided as a transport casing and is configured to be removed by the user before use of the auto injector 10. The rigid needle shield removal part 200 preferably cooperates with the casing 100 and the rigid needle shield 300 so that the rigid needle shield may be easily removed with the casing 100.

The auto injector has a housing 400 configured to enclose the further auto injector parts, including the syringe lock 500 and the skin sensor 600 which parts cooperate to release and lock the needle shield and the syringe assembly. The skin sensor driver 700 may be a spring. The syringe tube is provided to accommodate the syringe 900 with needle 902, and is interconnected to the plunger rod tube 1 100. A sound generator 1000 is positioned in-between the syringe 900 and the plunger rod tube 1 100. A syringe driver 1200 is configured to act on the syringe 900 in the syringe tube 800. Housing lock ring 1300 interconnects the housing 400 and reload handle top 1800. The handle 1400 is interconnected with the handle top 1800 and allows for reloading of the device, in co-operation with syringe lock 500 and skin sensor 600 as further described below. The plunger rod 1500 comprises a plurality of teeth 1502 configured to generate sound while moving in relation to sound generator 1000. Plunger rod driver 1600 is configured to apply a force to the plunger rod 1500. Torsion ring 1700 transmits the rotational movement of the handle top to a translational movement of the syringe assembly. Handle top 1800 is positioned at an end of the auto injector 10, and is configured to be rotated with respect to the housing 400 upon reloading of the device.

FIG. 2 illustrates the auto injector in various use states as seen from the point of the user or patient. In FIG. 2A, the auto injector is enclosed in casing 100 and the casing 100 is adjoining handle top 1800. In FIG. 2B, the casing 100 is removed and auto injector 10 has become visible. The auto injector 10 comprises housing 400 having an inspection window 402 and a skin sensor 600. A medicament 904 in the syringe 900 is visible through the inspection window 402, as indicated by the dark color of the window thereby indicating to a user that the auto injector is ready to use. The handle top 1800 is configured to interact with reload handle 1400 which is partly visible below the handle top 1800 in FIG. 2B. The skin sensor 600 is in an extended forwards position, completely shielding the needle. In FIG. 2C, the skin sensor is pushed slightly backwards in relation to the skin of a patient, and the needle 902 is visible in the skin sensor opening 602. The automatic needle insertion is not yet activated. In FIG. 2D, the skin sensor 600 is pushed backwards and is in the retracted position, and the automatic needle insertion has been activated so that needle 902 protrudes from the skin sensor and the tip of the syringe 900 is visible in the skin sensor opening 602. In this position, the needle is configured to be inserted into the skin of a patient. When the user removes the needle 902 from the skin after injection, the skin sensor 600 is pushed forward and shields the needle 902. The needle sensor is in a locked position. It is seen that in neither of the FIGS. 2C to 2E is the medicament visible through the inspection window 402 thereby indicating to a user that the device is not in an initial position ready to deliver a dose. In FIG. 2F, the auto injector 10 is re-loaded by turning the handle top 1800 with respect to the housing 400, the skin sensor is in an unlocked position and the medicament 904 in the syringe 900 is visible through the inspection window 402. In FIG. 2G, the skin sensor is in a locked position after a second dose has been delivered, and the inspection window 402 indicates that the device is not in a ready position.

Figures 3A, 3B, 3C:
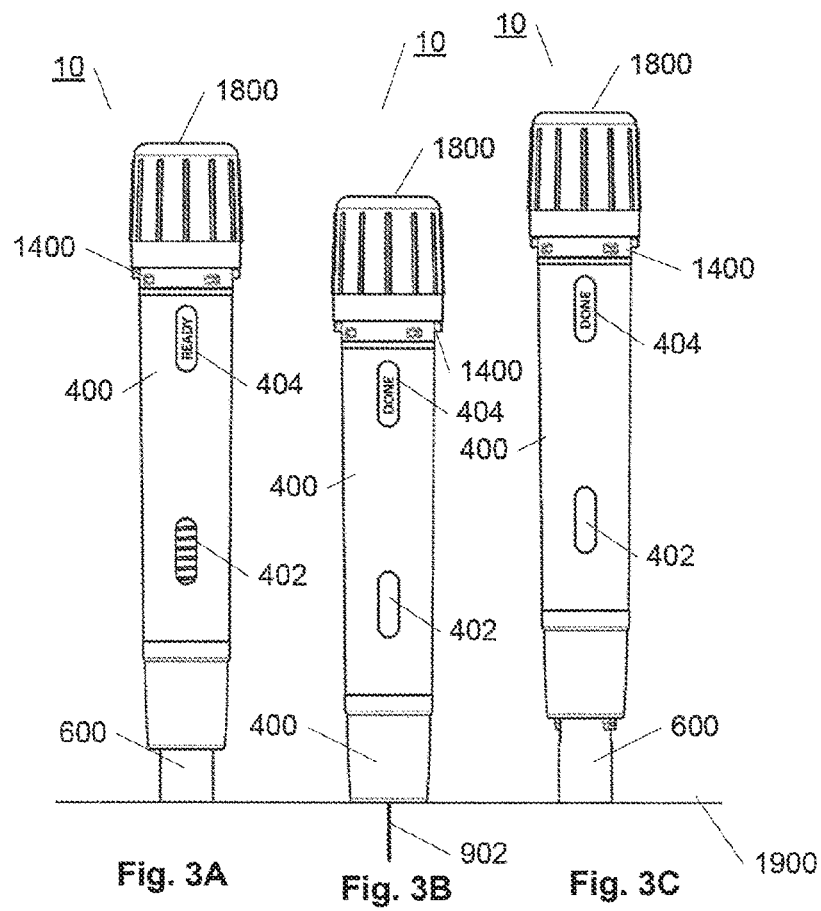
FIGS. 3A-C show indicators in different states.

In FIG. 3, indicator windows 402, 404 are provided. The inspection window 402 and the label window 404 of auto injector 10 is shown in more detail. In FIG. 3A, the auto injector is in a ready state with the cap and casing removed. The inspection window is open and thus exposes the medicament 904 in the syringe 900 and the skin sensor driver 700 is furthermore visible through the window. It is seen that the skin sensor is in the unlocked forward position and the device is ready to deliver a dose, as is also indicated by label window 404 reading "READY". In FIG. 3B, the needle 902 has been injected into a patient's skin 1900. The skin sensor is fully retracted and the housing 400 is resting on the patient's skin 1900. The inspection window is closed and does not reveal the medicament, and the label window has the reading "DONE" when the dose has been injected. In FIG. 3C, the skin sensor is fully extended and is in the locked forward position and skin sensor lock tabs 608 are visible. The inspection window is closed and the label window still has the reading "DONE". It is seen that during the injection process, the needle 902 is not visible for the user or the operator activating the auto injector and the skin sensor also acts as a needle shield or needle shroud. It is seen from the FIGS. 2 and 3 that the overall length of the auto injector is not significantly increased when delivering a further dose and it is an advantage of the present invention that a compact auto injector is provided which is capable of delivering one or more doses. The compact size is obtained due to the reversible features of the auto injector as further described below.

FIG. 4 shows the mechanism for removing casing 100 in more detail. As seen in FIG. 4A, the casing 100 is adjoining the handle top 1800. The casing may be held in place by a ring snap mechanism in place between the handle 1400 and the casing 100. The casing 100 and the handle top 1800 may be sealed by a piece of adhesive tape (not shown) wrapped around the casing 100 and handle top 1800 assembly. Upon activation, that is when the user unpack the auto injector 10, the casing 100 is removed from the auto injector 10 by twisting it slightly against the handle top 1800, utilizing a tapered knob 1402 on the auto injector, such as on the reload handle 1400 to translate the rotational force into a longitudinally movement which breaks adhesive as shown in FIG. 4B. In FIG. 4B, in which the casing is slightly turned to break the seal and disengage the ring snap mechanism. The casing 100 is removed partly by the rotation and partly by the longitudinal displacement following both the longitudinal movement initiated by the tapered knob 1402 and a pulling action initiated by the user.

In FIG. 5, The RNS (Rigid Needle Shield 300 covers the stacked injection needle 902 on the syringe 900 and is typically pre-mounted on the syringe 900 before entering a device assembly line. To ready the auto injector 10 for injection, the rigid needle shield needs to be removed to expose the needle. The removal of the RNS 300 is an integrated part of the auto injector activation process and hence automated in view of the operator or user. The RNS removal part 200 may be provided so that the auto injector 10 including the RNS 300 is not tampered with during storage. Preferably, the RNS 300 may be protected so that any significant physical dislocation from the initial sealing position of the RNS 300 is avoided. Such physical dislocation could be e.g. a radial or a longitudinal displacement and could be caused by rocking motions etc.

These physical dislocations could have a serious impact on auto injector performance and could e.g. bend the injection needle 902. The process of removing the RNS 300 needs to be robust and reliable but at the same time, the seal provided by the RNS 300 should be efficient. Thus, the automated removal of the RNS 300 upon activation or unpacking of the auto injector 10 may ensure none or minimal physical interaction from outside forces to the RNS 300 during the storage period. Still, upon device activation the RNS removal may be highly robust as otherwise it may potentially be difficult for the operator to gain access for manual removal. Thus, the mechanism interfacing to the RNS 300 have to satisfy two opposite requirements. Furthermore, the assembly of the auto injector with the RNS removal part 200 should be easy and intuitive.

In FIG. 5A, the parts are shown in detail and the RNS removal part 200 has a general cylindrical shape and has slits 202 along its side to allow for insertion of the entire RNS 300. Furthermore, the RNS removal part 200 has a U-shaped cut-out 204 on the end surface towards the syringe 900 in order to allow the presence of the syringe 900, and the diameter/size of the U-shaped cut-out 204 may be designed to be smaller than the maximum diameter of the RNS 300 but large enough to not be in physical contact during storage, i.e. not touch upon syringe 900 or upper portion of the RNS 300. With the RNS removal part 200 in place, a longitudinal force pulling away from the syringe will now ensure engagement between RNS removal part 200 and the larger diameter rime on the RNS 300 and may thereby force the RNS 300 to be pulled off of the syringe 900.

The RNS removal part 200 is in the present embodiment applied sideways with respect to the RNS 300 and syringe assembly 900, and FIG. 5B shows the RNS removal part 300 applied sideways to the RNS 300. In this embodiment, the RNS removal part 200 does not comply with the otherwise axially stacked assembly of the auto injector. FIG. 5C shows the syringe 900 with the RNS removal part 200 and the skin sensor 600 mounted on circumferential to the RNS removal part 200.

To benefit from the described RNS removal part 200, a fixation between the RNS removal part 200 and the casing 100 is suggested by heat stacking. In FIG. 5D, a cross section of the interface between casing or cap 100 and the RNS removal part 200 is shown as mounted, the RNS removal part tip 206 is shown extending beyond the casing 100. In FIG. 5E, it is seen that heat stacking has been applied and the RNS removal part tip 206 has been deformed to fixation part 208. It is however envisaged that any other means of fixation would be possible, e.g. a screw or a rivet, using ultrasonic welding etc.

Due to the fixation between the rigid needle shield removal part 200 and the casing 100, the RNS removal part will move when the casing is moved. Thus, due to the longitudinal displacement initiated by the twisting and pulling action applied to the casing 100 with respect to handle top 1800, the RNS removal part 200 will start to pull off the RNS 300 where the remaining dismantling of the RNS 300 is carried out by the operator or user. The gearing by the rotation over the tapered knob 1402 helps the operator or user to more easily overcome potential high stick-forces for the RNS 300 after longer time of storage; once the RNS 300 has been moved a small distance, the operator may easily pull off the RNS 300 the remaining distance, to free the needle 902 completely, at much less force input. It is envisaged that also other way of generating a longitudinal movement from rotation may be used instead of tapered knob 1402, e.g. by an internal thread where unscrewing in one predetermined rotational direction would yield longitudinal separation between the handle and casing. Use of the tapered knob 1402 has an advantage over internal hidden features in that it helps during assembly of the auto-injector device as there is a visually clear rotational orientation for the two parts to meet.

FIG. 6 shows a cross sectional view of an auto injector in a number of injection stages. In FIG. 6A, the auto injector is in a storing stage. The auto injector 10, apart from the handle top 1800 is encompassed in casing 100. The RNS 300 and the RNS removal part 200 are in position to protect the needle 902 and facilitate removal of the RNS, respectively. The plunger rod 1500 is in an initial position and a forward end 1510 of the plunger rod 1500 is positioned at a distance from a syringe stopper 908 surface. Thereby, a slight accidental movement of the plunger rod 1500 will not impact the syringe stopper 908.

Figure 6A:
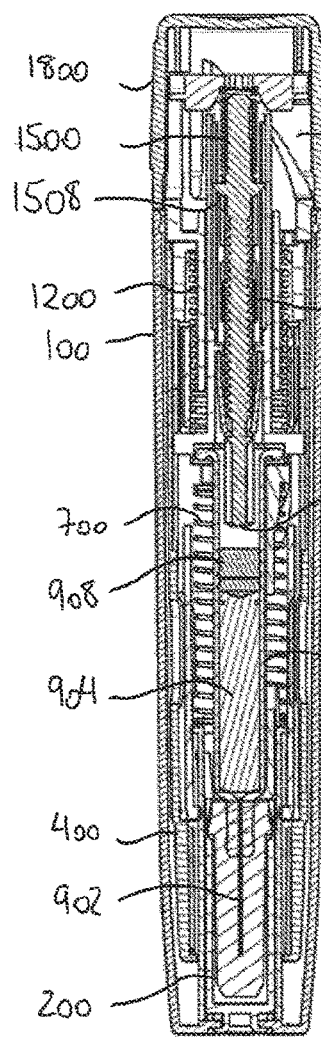
FIGS. 6A-E show a cross sectional view of an auto injector according to the invention during different stages of operation.
Figure 6B:
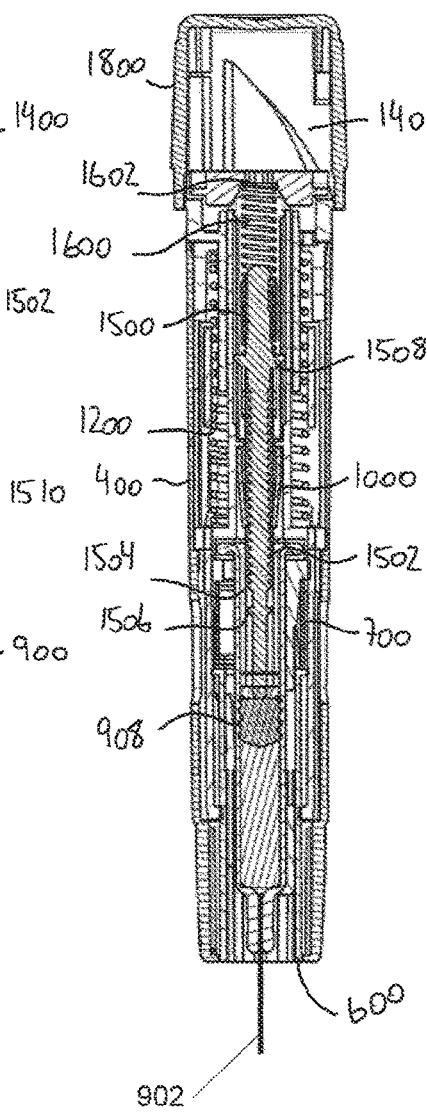

In FIG. 6B, the auto injector is shown immediately after the injection of a first dose.

Figure 7:
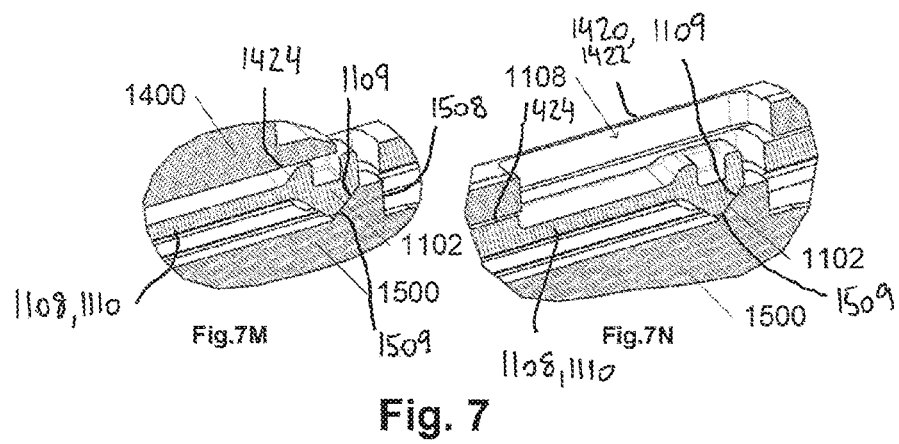
FIGS. 7A-N show a reload handle, plunger rod tube and plunger rod in various stages.

The needle 902 is exposed and inserted into the skin of a patient (not shown) and the plunger rod 1500 has been moved forward under influence of plunger rod driver, i.e. spring, 1600, so that the protrusion 1508 of the plunger rod rests against a first stop 1 102 of the plunger rod tube 1 100, see further details in FIG. 7. The stopper 908 has been moved forward to expel a first dose of medicament and the skin sensor 600 is the retracted position.

Figure 6C:
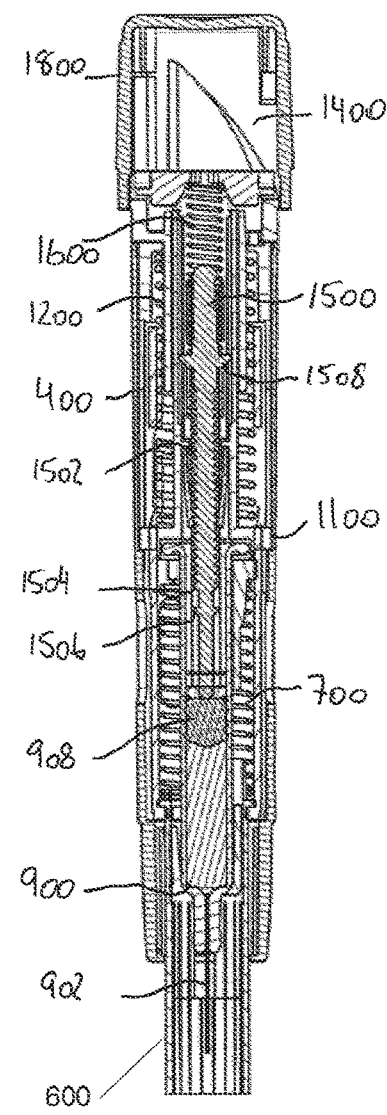

After the needle 902 has been retracted from the skin, in FIG. 6C, the skin sensor 600 is moved to a forward locked position by skin sensor driver 700. At the stage C in FIG. 6C, the auto injector may be either discarded as it is or reloaded for delivering of a second or further dose.

Figure 6D:
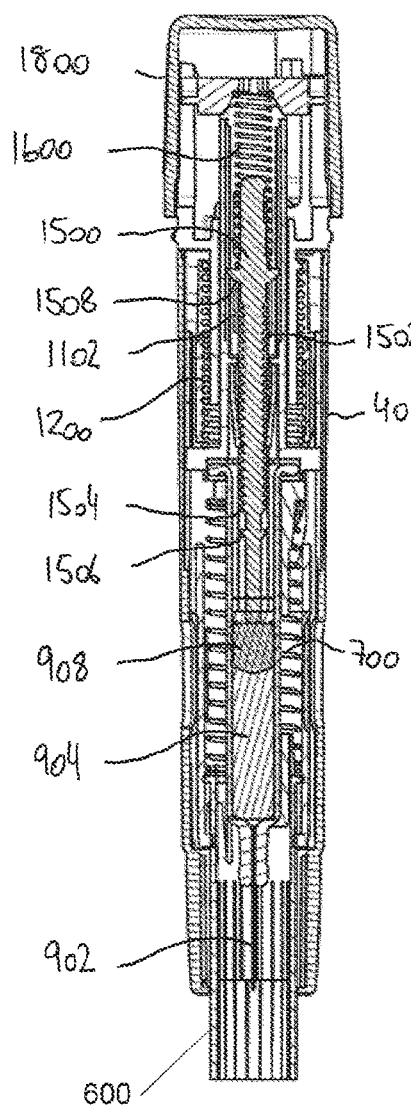

FIG. 6D shows the auto injector 10 after reloading of the device: The plunger rod 1500 has been moved forward under influence of plunger rod driver, i.e. spring, 1600, so that the protrusion 1508 of the plunger rod rests against a second stop 1 104 of the plunger rod tube 1100, see further details in FIG. 7. The stopper 908 has been moved forward to expel a first dose of medicament and the skin sensor 600 is the retracted position.

The skin sensor 600 has been unlocked and is in the forward unlocked position, the syringe driver 1200 has been reloaded, i.e. retracted, into an initial compressed position and the syringe 900, the syringe tube 800, the plunger rod tube 1 100, the plunger rod 1500 and the plunger rod driver 1600 have been retracted without moving the mentioned parts in relation to each other.

Figure 6E:
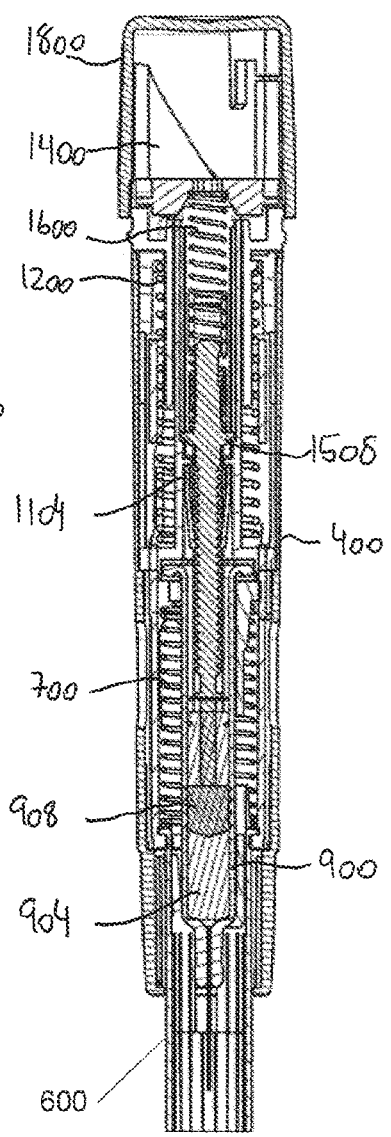

In FIG. 6E, a second or further injection has been made. The plunger rod 1500 has been moved forward under influence of plunger rod driver, i.e. spring, 1600, so that the protrusion 1508 of the plunger rod rests against a second stop 1 104 of the plunger rod tube 1 100, see further details in FIG. 7. The stopper 908 has been moved forward to expel a second or further dose of medicament. The skin sensor 600 is in the forward locked position and the auto injector may be discarded, a further injection may be performed or the auto injector may be re-used by for example re-fitting the auto injector with a new pre-filled syringe.

In FIG. 6, it is seen that the plunger rod driver 1600 comprises a plunger rod spring 1600. The plunger rod spring 1600 is in one end 1602 fixedly connected to the plunger rod tube 1 1001 is seen that the plunger rod driver 1600 applies the driving force directly onto the plunger rod 1500, such as onto a plunger rod flange 1508, i.e. the plunger rod protrusion 1508. In FIG. 6, it is seen that the plunger rod driver acts on the top of the plunger rod flange 1508 whereas the other side of the plunger rod flange 1508 normally locks the plunger rod 1500 to the plunger rod tube 1 100, in that the plunger rod stop 1508 presses on the locking member 1 108, i.e. presses on the plunger rod tube stop 1102.

The housing further accommodates a syringe tube for holding the syringe, and the syringe has a syringe flange which is locked between the syringe tube and the plunger rod tube. In the present example, the syringe tube and the plunger rod tube are provided as two separate units to ease assembly, however, it is envisaged that the syringe tube and the driver rod tube may be one tube holding the syringe, the plunger rod and the plunger rod driver.

It is seen that the plunger rod driver is provided inside the plunger rod tube, and the syringe driver is provided outside the plunger rod tube.

In FIGS. 7A-L, a reload handle and the cooperation with the plunger rod tube and the plunger rod is shown. Only a top portion 30 of an auto injector as e.g. seen in any of the FIGS. 1-6 above or any of the figures is seen in FIG. 7. The auto injector as shown in FIG. 7, is capable of sequentially control the needle insertion and dose injection. The function of the sequential control is illustrated in stages A through L.

FIGS. 7A, 7C, 7E, 7G, 7I and 7K shows the reload handle 1400, the plunger rod tube 1 100 and the plunger rod 1500 in various stages of the process, and FIGS. 7B, 7D, 7F, 7H, 7J and 7L show a cross-sectional view of the auto injector in the stages A, C, E, G, I and K.

The plunger rod 1500 is configured to be advanced in the syringe (not shown in FIG. 7) for delivering at least one dose of medicament. The plunger rod tube 1100 has a least one locking member 1 108 configured to interact with a plunger rod stop 1508 to normally lock the plunger rod 1500 to the plunger rod tube 1 100 (see FIGS. 7M, 7N). The syringe driver 1200 is not shown in FIG. 7, however the activation of the syringe driver is illustrated by the arrows 42, 44, that is the plunger rod tube 1 100 and the plunger rod 1500 are both moved forwards, i.e. from the first position to the second position. The plunger rod driver 1600 is not shown in FIG. 7, however, the activation of the plunger rod driver 1600 is illustrated by single arrow 42 illustrating that only the plunger rod is moved forward, i.e. the force applied by the plunger rod driver 1600 forces the plunger rod 1500 to advance in the syringe (not shown) for delivering at least one dose of medicament. It is seen that the housing 400, or in the present case an intermediate element 1400, i.e. the reload handle 1400, comprises an opening or an aperture 1420. The housing or intermediate element 1400 is configured to unlock the locking member 1 108 and release the plunger rod 1500 from the plunger rod tube 1 100 when the syringe (not shown) and the plunger rod tube 1 100 is advanced to the second position, thereby activating the plunger rod driver (not shown) to advance the plunger rod 1500 in the syringe for delivering of at least one dose of medicament.

The locking member 1 108 comprises at least one deflectable member 1 108 and the housing 400 and/or the intermediate member 1400 is configured to allow for the at least one deflectable member 1 108 to deflect away from the plunger rod 1500 when the syringe (not shown) and the plunger rod tube 1 100 is advanced to the second position. Thus, it is seen in FIGS. 7A, 7B that the plunger rod 1500 in the plunger rod tube 1 100 is in an initial position, i.e. a first position, ready to deliver a dose of medicament. In the second position after forwards movement of the plunger rod tube 1 100 and the plunger rod 1500, the plunger rod tube is in the second position. It is seen in FIGS. 7C, 7D, that the plunger rod 1500 has not been moved with respect to the plunger rod tube 1 100 and both the plunger rod tube 1 100 and the plunger rod 1500 has been moved forwards relative to the housing or intermediate member 1400. The plunger rod driver is typically positioned inside the plunger rod tube 1100 circumferentially around a backward end 1512 of the plunger rod 1500 configured to apply a force to the plunger rod protrusion 1508. The backward end 1512 may have a reduced diameter, i.e. a diameter reduced relative to the diameter of other parts of the plunger rod, such as for example relative to the forward end of the plunger rod 1510.

The plunger rod tube 1 100 and the syringe (not shown) are typically interconnected so that the plunger rod tube 1 100 cannot move with respect to syringe 900 and vice versa. The plunger rod tube 1 100 may be interconnected to the syringe 900 or the syringe tube 800, for example via plunger rod tube tabs 1 1 10.

The housing has an opening 1420, the opening 1420 being a window, or an aperture, configured to be aligned with the at least one deflectable member when the plunger rod tube is advanced to the second position. In FIG. 7D, it is seen that the first deflectable locking member 1 108 is aligned with the window or aperture 1420 thereby allowing the locking member 1 108 to deflect and allow passage of the plunger rod protrusion 1508, such as the plunger rod stop 1508.

It is seen in FIG. 7E that upon release of the plunger rod 1500, the plunger rod driver 1600 advances the plunger rod 1500 within the syringe 900 in that the plunger rod stop 1508 is able to pass the deflected locking member.

A deflectable locking member 1 108, 1 1 10 is positioned at either side of the plunger rod as seen in FIG. 7B, and thus also the openings 1420, 1422 are provided on either side.

In FIG. 7G, the handle 1400 is rotated as illustrated by arrow 1401 and the plunger rod tube 1 100 with plunger rod 1500 is rotated and retracted to the same initial position as illustrated in FIG. 7A, while the plunger rod maintain the advanced position with respect to the plunger rod tube, and the plunger rod driver (not shown in FIG. 7) also maintaining a first extended position. From this position, a second dose delivery is performed, and FIGS. 7I and 7J illustrate the repeated forward motion of the plunger rod tube with the plunger rod, as illustrated by arrows 42, 44 so as to align the second window 1422 with the second deflectable locking member 1 1 10 and allow deflection of the locking member 1 1 10. Thereby, the plunger rod driver 1600 is released or activated to push the plunger rod 1500 pass the second locking member 1 1 10, for delivering of a second dose as illustrated by single arrow 42, and FIGS. 7K, 7L illustrates the plunger rod in the advanced position within the syringe. The plunger rod driver is thus configured to move the plunger rod 1500 a first distance upon a first activation of the plunger rod driver 1600, and a further distance upon a further activation of the plunger rod driver 1600.

It is seen that the second activation of the plunger rod driver follows a reload of the auto injector, and thereby a repeated movement of the syringe assembly 20, i.e. such as syringe 900, syringe tube 800, plunger rod 1500, and plunger rod tube 1 100 from the first position to the second position.

Thus, the auto injector may deliver at least one or two separate doses of medicament.

It is seen in FIGS. 7M, 7N that the plunger rod stop has an angled surface 1509 normally pressing against an angular surface 1 109 of the deflectable locking member 1 108. The deflectable locking member 1 108, 1 1 10 is hinged to the plunger rod tube 1 100 in a downward position with respect to the movement of the plunger rod.

Hereby, the deflectable locking member may deflect only when the entire length of the deflectable locking member 1 108, 1 1 10 opposes the full opening 14.

The at least one deflectable member is configured to deflect upon being aligned with the opening in the housing 400 and/or the intermediate member 1400.

When the deflectable locking members 1 108, 1 1 10 are not aligned with the window 1420, the deflectable locking members 1 108, 1 1 10 are typically prevented from deflection by an inner surface 1424 of the handle 1400 or housing 400, and it is seen in FIG. 7N that the deflectable locking member 1 108, 1 1 10, is not entirely within the window 1420, 1422 and therefore not able to deflect.

The plunger rod tube 1 100 may thus comprise at least a first and a second locking member 1008, 1 1 10 configured to engage with the plunger rod stop 1508.

Figure 8:
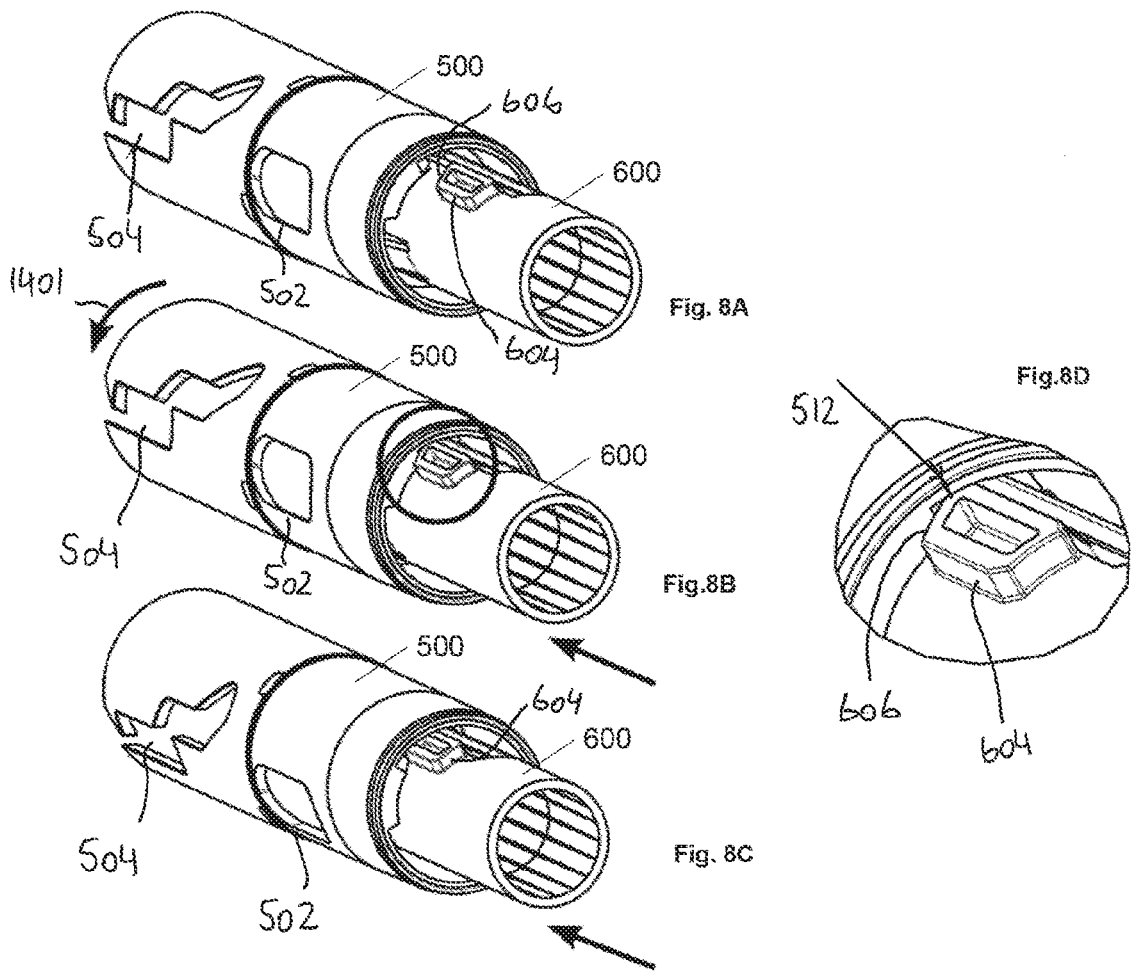
FIGS. 8A-C show details of a skin sensor.

FIG. 8 shows the skin sensor 600 and the interaction of the skin sensor 600 with syringe lock 500 in more detail. In FIG. 8A, the skin sensor 600 and the syringe lock 500 are in their initial positions, and the skin sensor 600 is thus in the forward unlocked position. A protrusion 604 having an angled surface 606 is seen at the skin sensor 600. In FIG. 8B, the skin sensor 600 is activated, by e.g. pressing the skin sensor 600 against the skin of a patient, and the skin sensor 600 is moved towards the syringe lock 500. Hereby, the angled surface 606 engages with a syringe lock angled surface 512 to thereby force the syringe lock 500 to rotate while the skin sensor 600 is retracted. In FIG. 8C, the skin sensor 600 is fully depressed, i.e. fully retracted, and engaged with the syringe lock after rotation. FIG. 8D shows a detailed view of the syringe lock protrusion 604 and the angled surface 504 of the syringe lock 500.

Figure 9:
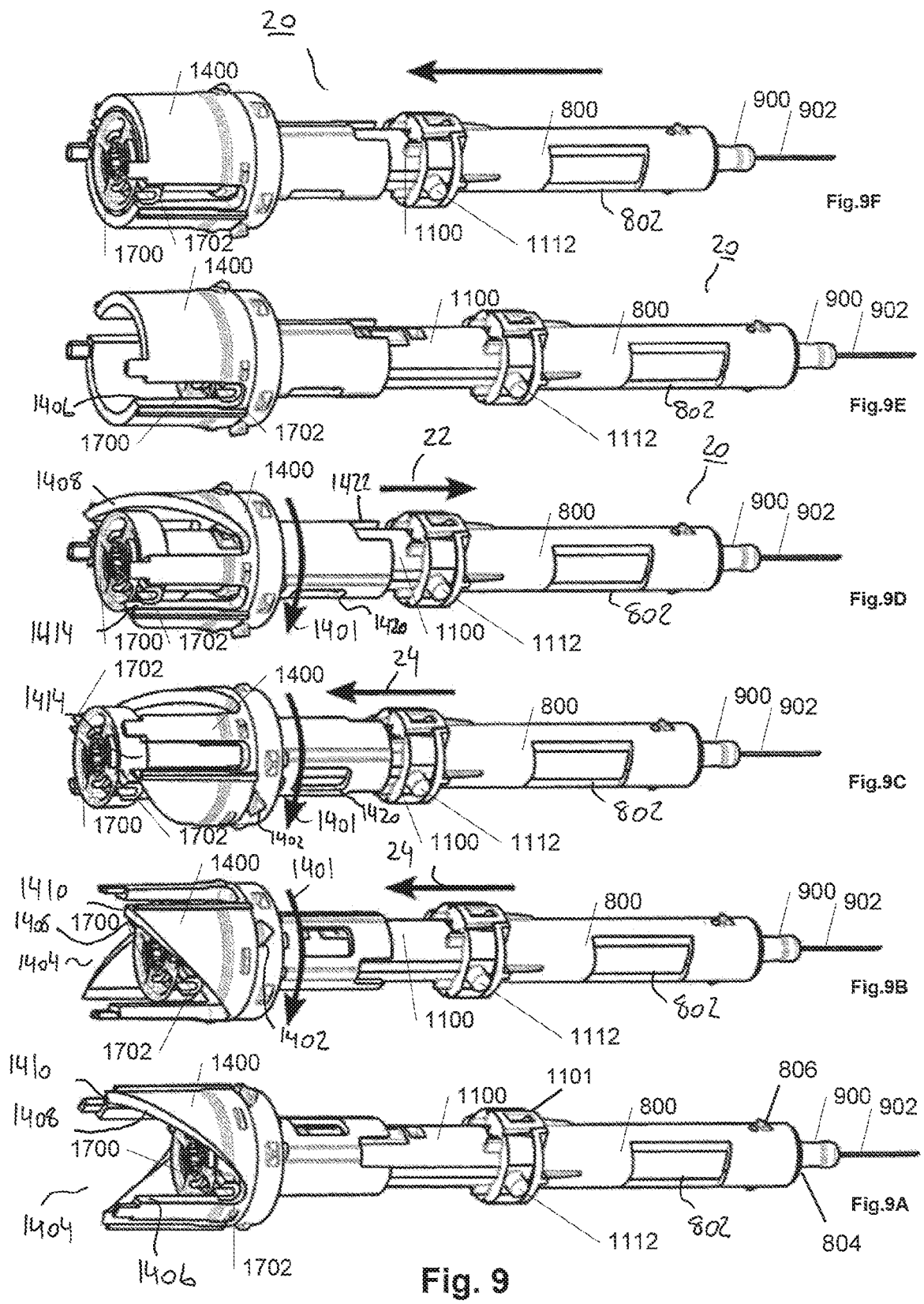
FIGS. 9A-F show a reloading mechanism according to the present invention.

In FIG. 9, a reloading mechanism is shown in more detail. In FIG. 9A (bottom of the figure), the syringe 900 with needle 902 is seen projecting from syringe tube 800 in a first end, such as a forward end, 804. The syringe tube 800 is engaged with plunger rod tube 1 100 and tabs 1 1 10 on the forward end 1 101 of plunger rod tube 1 100 engages with the syringe tube 800 to interconnect the plunger rod tube 1100 and the syringe tube 800. Typically, during assembly, the pre-filled syringe 900 with needle 902 will be inserted into syringe tube 800 and plunger rod tube 1 100, comprising plunger rod 1500 and plunger rod driver 1600, will be mounted onto the syringe 900 and syringe tube 800 and the lips 910 of the syringe will be locked between the syringe tube 800 and plunger rod tube 1100. A tab 1 1 12 on the plunger rod tube 1 100 is configured to interact with syringe lock 500 (see FIG. 10 for further details). The syringe tube 800 has a syringe tube inspection window 802 configured to interact with syringe lock inspection window 502 and housing inspection window 402. Syringe tube protrusions 806 may interact with skin sensor 600 and provide an initial force which must be overcome by the user when activating the auto injector. This is a further safety feature which reduces the risk of accidental activation of the auto injector.

Reload handle 1400 is slided onto plunger rod tube 1 100 and torsion ring 1700 interconnects reload handle 1400 and plunger rod tube 1 100 via torsion ring tab 1702.

In FIG. 9A, a first dose has been delivered and it is seen that torsion ring tab 1702 is provided in a first reload handle slot 1404, and the torsion ring tab 1702 has moved forwards along slot side 1406 and is positioned at the bottom of the first reload handle slot 1404.

The reload handle 1400 as well as torsion ring 1700 may be symmetric, so as to evenly distribute the force applied, and that there is thus a torsion ring tab 1702 provided symmetrically on each side of the torsion ring, each torsion ring tab 1702 interconnecting each of the first reload handle slots provided symmetrically about the reload handle slot.

In FIG. 9B, the reload handle 1400 is rotated as indicated by arrow 1401, thereby forcing the torsion ring which cannot rotate itself, along the inclined slot side 1408 via torsion ring tab 1702. In FIG. 9B, it is seen that the torsion ring tab 1702 has moved slightly along the inclined slot side 1704 after having rotated the reload handle slightly, e.g. about 30 degrees, as seen by the rotation of the reload handle tapered knob 1402. This pulls the syringe assembly comprising the syringe 900, syringe tube 800, plunger rod tube 1 100, as well as plunger rod 1500 and plunger rod driver 1600 (not shown in FIG. 9) backwards and into the reload handle 1400 as illustrated by arrow 24.

In FIG. 9C, the reload handle is further rotated, e.g. rotated 45 degrees in total, and the torsion ring tab 1702 has moved towards the top edge 1410 of the first reload handle slot 1404 further retracting the syringe assembly 20 comprising syringe 900, syringe tube 800, plunger rod tube 1 100, as well as plunger rod 1500 and plunger rod driver 1600 (not shown in FIG. 9) backwards and further into the reload handle 1400. While rotating the reload handle 1400 the plunger rod tube tabs 1 1 12 also rotates towards a resting ledge 506 of the syringe lock 500, as may be seen from FIG. 10.

As seen in FIG. 9D, continued rotation of the reload handle 1400 lifts the torsion ring tab 1702 together with torsion ring 1700 and syringe assembly 20 over the top edge 1410 of the first reload handle top 1400 and into second reload handle slot 1414. The torsion ring 1700 including the torsion ring tab 1702 and the syringe assembly will move forward a short distance, such as a few mm, as indicated by arrow 22, before the syringe assembly 20, and more specifically, the plunger rod tube tabs 1 112 hang on the syringe lock resting ledge 506. The auto injector 10 is then in the initial position and ready to deliver a second or further injection. In that the second reload handle slot is a slot allowing only for movement longitudinally along an axis of the auto injector, the auto injector is locked after having delivered a second dose, and the auto injector is thus not configured to deliver more than two doses. Thus, the auto injector may deliver no more than two doses. Also, alternative configurations have been envisaged and this is shown in further detail in FIG. 13.

FIGS. 9E and 9F illustrates an alternative reload function in which the reload system relies on a longitudinal retraction of the syringe assembly 20, and FIG. 9E illustrates the reload handle 1400 and torsion ring tab 1702 position after a first injection has been delivered. In FIG. 9F, a longitudinal retraction of the syringe assembly 20 reloads the auto injector.

Figure 10:
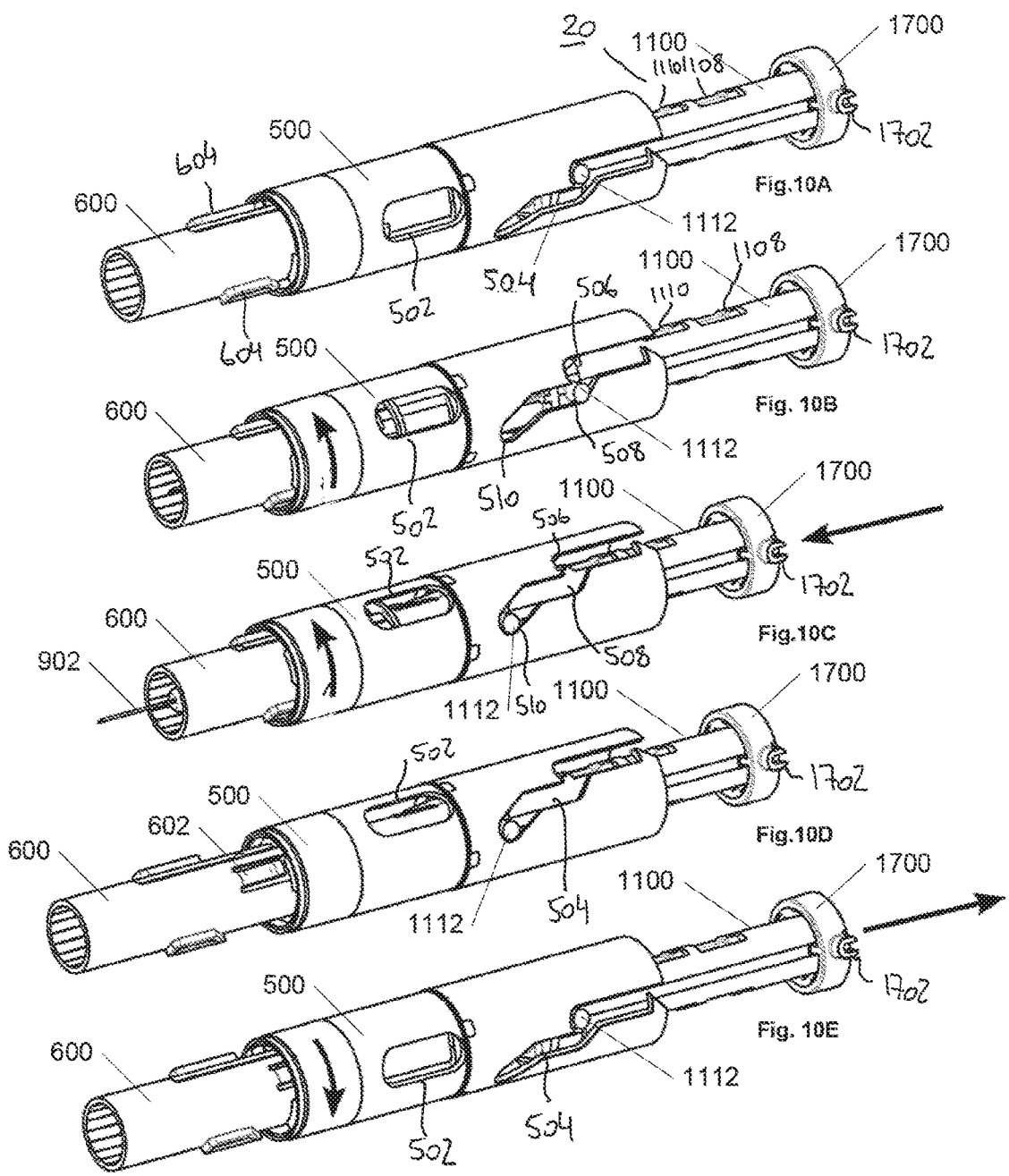
FIGS. 10A-E show a syringe lock guiding trail in various stages, FIGS. 11 A-B show a detailed view of an inspection window.

FIG. 10 shows a detailed view of the syringe lock guiding trail 504 enabling the skin sensor 600 to rotate the syringe lock 500 and control the dosing mechanism. Initially, as seen in FIG. 10A, the spring loaded syringe assembly 20 rests on a syringe lock resting ledge 506 in the syringe lock 500 by plunger rod tube tabs 1 1 12, restricting forward movement of the syringe assembly 20. The skin sensor 600 is in the unlocked forward position.

In FIG. 10B, the skin sensor is pressed against the skin of a patient, and the syringe lock is rotated as indicated by arrow 24. Hereby, the syringe assembly 20 is lifted free of the syringe lock resting ledge 506.

In FIG. 10C, the syringe assembly 20 has moved downwards along syringe lock guiding trail 504, pushing the syringe assembly 20 forwards causing injection of needle 902. During injection of the needle, the syringe lock is further rotated to align dosing clips with dosing windows to allow for injection of a medicament. After injection, as seen in FIG. 10D, and as the needle 902 is retracted from the skin of a patient, the skin sensor 600 is pushed forward by skin sensor driver 700. At this point, the two clips of the skin sensor are resting on a shelf on the syringe lock, locking them in position to protect the needle. In FIG. 10E, the device is reloaded and the syringe assembly 20 is in the initial position and the skin sensor 600 in the forward unlocked position.

Figure 11A:
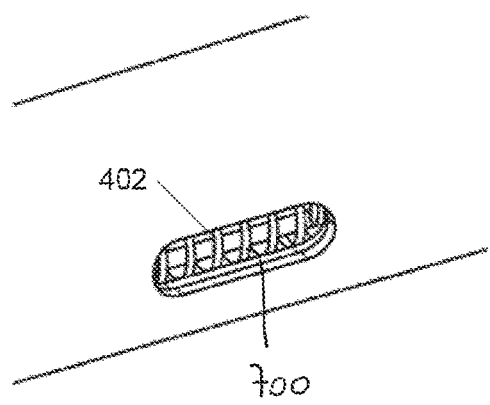
Figure 11B:
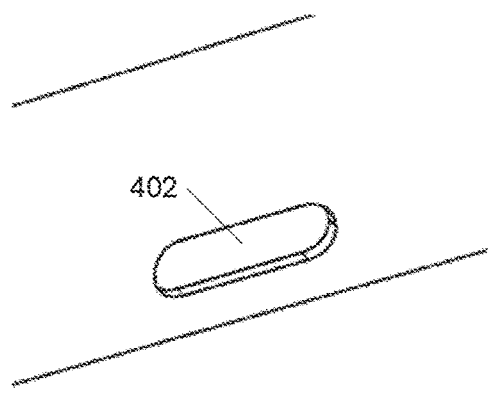

FIG. 11 shows a detailed view of the inspection window 402. In FIG. 11 A, housing inspection window 402, syringe tube inspection window 802 and syringe lock inspection window 502 are aligned and the medicament 904 in the syringe 900 is visible. Furthermore, the skin sensor driver 700 is visible through the housing inspection window 402 and the syringe lock inspection window 502. In FIG. 1 1 B, it is seen that the inspection windows are not aligned and that only a part of the syringe lock 500 is visible behind the housing inspection window indicating that the device is not ready for delivering an injection dose.

It is an advantage that a user or patient is able to see the medicament through the inspection windows 402, 502 and 802 at the time of injection of the medicament, as it gives the user a sense of what is injected.

Figure 12A:
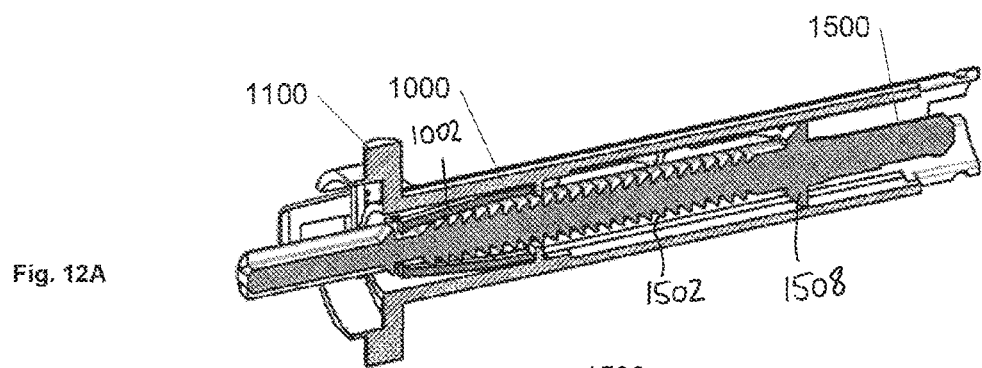
FIGS. 12A-C show a sound generator.
Figure 12B:
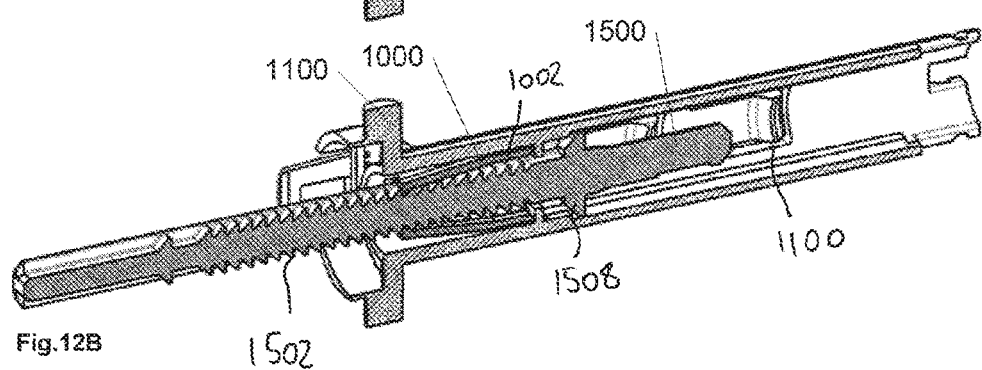
Figure 12C:
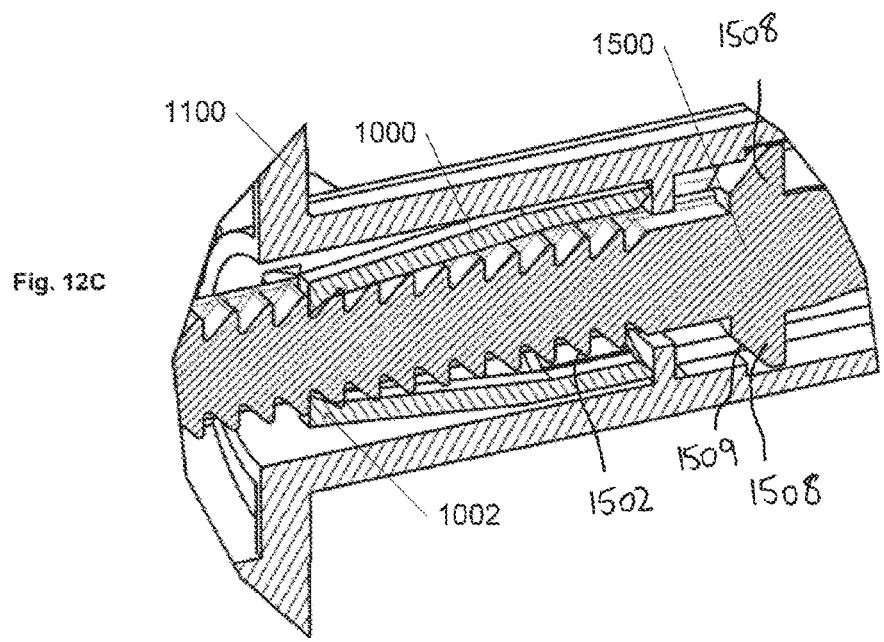

In FIG. 12, a ratchet mechanism comprising a plunger rod 1500 interacting with a sound generator 1000 is shown. The sound generator 1000 comprises flexible arms 1002 positioned with the syringe assembly 20 and configured to engaged sloped teeth 1502 of the plunger rod. The upwardly sloped teeth 1502 on the plunger rod may allow forward movement of the plunger rod only.

It is seen that the ratchet mechanism 1500, 1502, 1000, 1002 is configured to provide a sound while delivering a medicament, so that a sound is generated while dosing. The sloped teeth are provided along the length of the plunger rod, and substantially along the entire length of the plunger rod so that the sound is generated during delivery of a first dose and during delivery of a second dose and/or any further doses. It is however envisaged that the sloped teeth may be distributed over only a part of the plunger length and for example be configured to only generate a sound during delivery of the first dose, the second dose, any further doses or a last dose of medicament from the syringe to indicate end-of-medicament in a syringe.

It is an advantage of generating a sound during at least a part of the delivery of the dose, to thereby indicate with a sound when medicament is injected, that is, the sound is provided while dosing, and when the sound stops, the user may have to keep the needle under the skin for a period of time.

The plunger rod 1500 as illustrated in FIG. 12 is thus a linear ratchet having a number of sloped teeth 1502 configured to interact with a number of flexible arms 1002 provided with the plunger rod tube 1 100 so as to engage with the plunger rod 1500 when the plunger rod 1500 is advanced forwards passing the flexible arms to thereby generate a sound.

In FIG. 12A, the plunger rod 1500 is shown in the plunger rod tube in an initial position, i.e. before dosing. In FIG. 12B, a first dose of medicament has been delivered, and the plunger rod 1500 has moved in a forward direction a distance corresponding to the first dose. It is seen that there is a sound delay while the plunger rod is moved from first stop 1506 to second stop 1504, indicating that the sound only starts, when the stopper 908 is moved forward and is delivering a medicament. The ratchet mechanism is shown in more detail in C, where flexible arms 1002 are clearly seen to engage with sloped teeth 1502 of the plunger rod 1500.

Because the ratchet mechanism 1500, 1502, 1000, 1002 allows movement in one direction only, it is prevented that the plunger rod 1500 is returned to the initial position. Thereby, it is avoided that a used auto injector is re-fitted with another syringe and offered to a new user. Thus, the ratchet mechanism 1500, 1502, 1000, 1002 further acts as an anti-tampering component.

Figure 13:
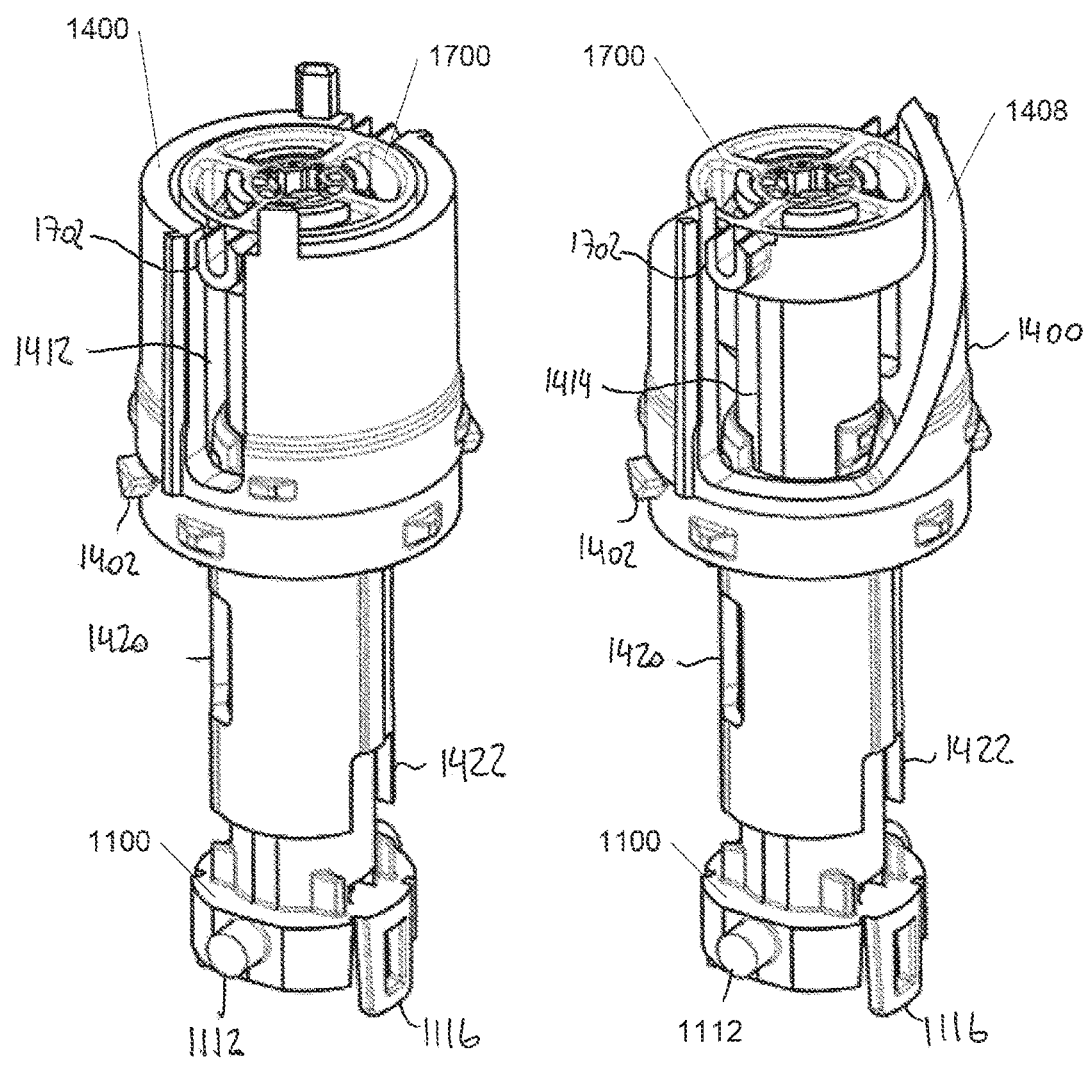
FIGS. 13A-B show a reload handle for single or repeated delivery of doses.

FIG. 13 shows two different reload handles in more detail. It is seen that the reload handle may be configured to allow for delivering of one, two, three, four or multiple doses. In FIG. 13a, a reload handle 1400 having a reload handle slot 1412 having two straight sides is provided, so that the reload handle slot allows for longitudinal movement along an axis of the auto injector only, and thereby does not allow for the rotational movement along an inclined surface. This means that only one injection is possible and that no reload function is available. It is seen that the auto injector is in the initial position with torsion ring tab 1702 at the top of the reload handle slot 1404. In FIG. 13b, a reload handle 1400 is shown having a reload handle slot 1414 having a straight side for the injection process and an inclined side 1416 which the torsion ring tab 1702 follows upon reloading. It is seen that the reload handle is provided with only two symmetric reload handle slots 1414, and that therefore an infinite number of reloads is possible as the rotation of the handle is never locked. This reload handle may for example be advantageous if the auto injector is re-usable and allows for refitting with for example a new syringe assembly. Any combination of the two reload handles as shown in FIG. 13a and FIG. 13b may provide any combination of a predetermined number of reloads following the slot design 1414 in FIG. 13b, followed by a locking slot 1412 not allowing for further reloads. The number of reload slots is primarily limited by the size of the auto injector.

Figure 14:
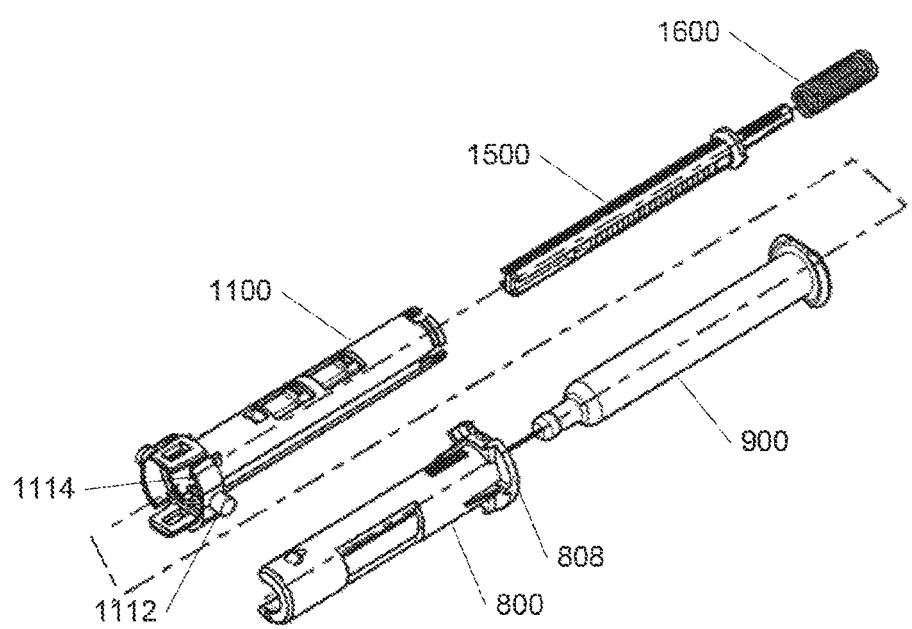
FIG. 14 shows a syringe assembly in more detail

In FIG. 14, a syringe assembly 20 is shown comprising syringe tube 800, syringe 900, plunger rod tube 1 100, plunger rod 1500 and plunger rod driver 1600. It is envisaged that the parts may be assembled using various connector parts, and furthermore, the plunger rod tube and syringe tube may be provided as one part. It is seen that the syringe assembly 20 may be moved as one element and either be pushed forward by a syringe driver (1200 not shown in FIG. 14) acting on syringe tube flange 806 and/or plunger rod flange 1 1 14 or retracted by a reload handle action acting on the syringe assembly 20, such as on the syringe assembly tab 1 1 12.

Figure 15:
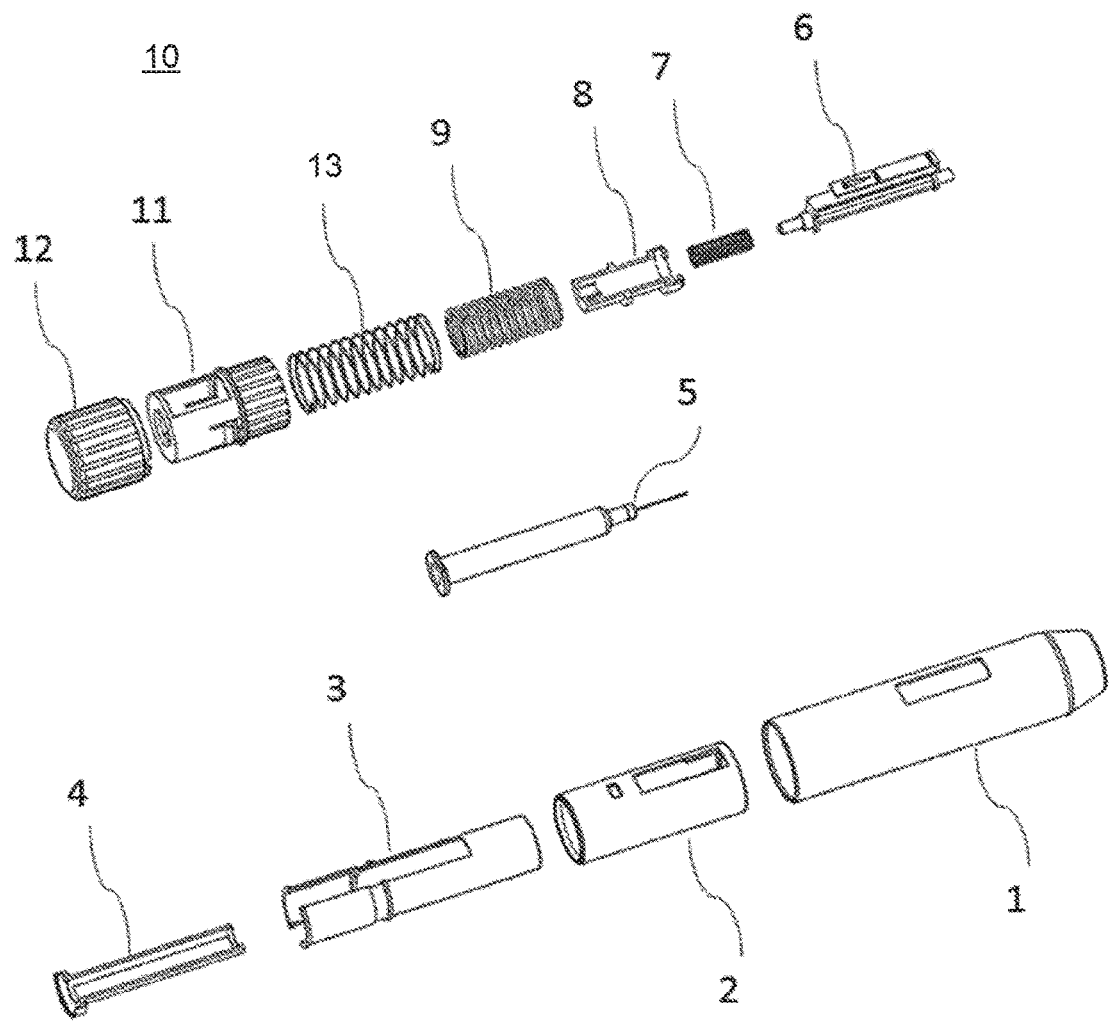
FIG. 15 shows another auto injector according to an embodiment of the present invention.

In FIG. 15, another auto injector according to an embodiment of the present invention is shown, comprising a cap or casing 1, a housing 2, a skin sensor 3, a syringe tube or holder 4, and syringe 5 having a rigid needle shield covering the needle in the stored position (not shown), a plunger rod 6 for acting on medicament in the syringe 5, a plunger rod driver, or motor spring, 7, a plunger rod tube 8 encompassing at least a part of the plunger rod driver 7 and of the plunger rod 6, and a syringe driver, such as motor spring, 9 configured to act on at least the syringe 5, and preferably on a syringe assembly comprising syringe tube 4, syringe 5, plunger rod 6, plunger rod driver 7 and plunger rod tube 8. A needle shield driver, such as a needle shield spring, 13, is configured to act on the needle shield/skin sensor 3. The auto injector further comprises a reload handle 1 1 and a reload handle top 12.

The auto injector 10 as unpacked is ready for use. The auto injector 10 is applied to the injection site, which pushes the needle shield 3 backwards a few millimeters. Hereby, the plunger rod tube acts to release the syringe driver 9 driving the plunger rod 6, and the plunger rod carrier or tube 8, and thereby syringe 5 forward resulting in the needle being inserted into the patient. When the needle is inserted, the plunger rod spring 7 is released resulting in a first dose being administered. The plunger rod 6 travels downwards until it hits a stop, which determines the dose size. Also, just before the plunger rod 6 comes to rest, the patient is given an audible feed in to signal "end of dose". Progression of the injection can also be observed through a window. After completion of an injection, the auto injector is lifted from the injection site and the needle shield 3 is extended forward by the use of the needle shield spring 10 and locks in its outer position where the combination of opening diameter and distance from the needle tip ensures sharps protection. The auto injector is now disabled and can either be re-mounted with the cap and disposed of or the auto injector can be prepared for an second injection if needed. Thus, the auto injector is ready for being prepared for the second injection. By turning the handle top 12, and thereby the reload handle 1 1, the plunger rod carrier or tube 8 and syringe carrier or tube 4 are retracted backwards. This is done by a detail on the plunger rod carrier 8 engaging in a thread inside the reload handle 1 1. When the handle has been pulled back, the plunger rod carrier 8 and the syringe carrier 4 disables itself. Further, when the reload handle is turned, it unlocks the needle shield 3 from its outer position, which enables the plunger rod carrier 8 and syringe carrier 4 to be moved forward when actuated.

When the auto injector is applied to the injection site, the needle shield 3 is pushed backwards a few mm, and thereby, the syringe carrier 4 is configured to release the insertion spring, or syringe motor, 9, thus driving the plunger rod 6 and the syringe carrier 4 forward resulting in the needle being inserted into the patient. When the needle is inserted, the injection spring, i.e. plunger rod driver, 7 is released resulting in the first (or second or any further) dose being administered. The plunger rod 6 travels downwards until it hits a stop, which determines the dose size. Also, just before the plunger rod 6 comes to rest, the patient or user is given an audible feed in to signal "end of dose". Progression of the injection can also be observed through a window. After a second or any further injection, the needle shield 3 is pushed forward by needle shield spring 13 as the needle is pulled back from the patient and the needle shield 3 locks in its outer position. In addition to this, the reload handle 1 1 is also disabled, meaning that the entire device is disabled and can safely be disposed off.

1 cap or casing
2 lower housing
3 needle shield
4 syringe holder
5 syringe with needle
6 plunger rod
7 plunger rod motor or driver
8 plunger rod carrier
9 syringe motor or driver
10 reloadable auto-injector
11 upper housing or reload handle
12 reload handle top
13 needle shield spring
20 syringe assembly
30 top portion of auto injector
22, 24, 42, 44 arrows
100 casing
200 RNS (rigid needle shield) remover
202 slit
204 U-shaped cut out
206 RNS (rigid needle shield) removal part tip
208 fixation part
300 RNS (rigid needle shield)
400 housing
402 inspection window
404 label window
500 syringe lock
502 syringe lock inspection window
504 syringe lock guide slot/trail
506 syringe lock ledge
508 a released position
510 syringe lock end stop.
512 syringe lock angled surface
600 skin sensor
602 skin sensor opening
604 protrusion
606 skin sensor angled surface
700 skin sensor driver
800 syringe tube
802 syringe tube inspection window
804 forward end
806 syringe tube protrusions
808 syringe tube flange
810 syringe tube connectors
900 syringe
902 needle
904 syringe content (medicament)
908 syringe stopper
910 lips
1000 sound generator
1002 flexible arms
1100 plunger rod tube
1101 forward end
1102 first stop of the plunger rod tube—locking member stop
1104 second stop of the plunger rod tube
1106 end stop position
1108 first locking member
1109 first locking member angled surface
1110 second locking member plunger rod tube tabs
1112 plunger rod tube tab/syringe assembly tab
1114 plunger rod tube flange
1116 plunger rod tube connectors
1118 back end of plunger rod tube
1200 syringe driver
1300 housing lock ring
1400 reload handle
1401 reload handle arrow
1402 tapered knob
1404 first reload handle slot
1406 slot side
1408 inclined slot side
1410 top edge of the first reload handle slot
1412 reload handle slot
1414 second reload handle slot
1420 first window
1422 second window
1424 inner surface
1500 plunger rod
1502 teeth
1504 second stop
1506 first stop
1508 protrusion of the plunger rod, plunger rod stop
1509 angled surface of plunger rod stop
1510 forward end of the plunger rod 1512 backward end of plunger rod
1600 plunger rod driver
1602 one end of plunger rod driver
1700 torsion ring
1702 torsion ring tab
1800 handle top
1900 skin barrier

The invention claimed is:

1. A reloadable auto injector comprising:
a needle insertion driver having a first spring and an injection driver having a second spring within a housing, wherein the reloadable auto injector is configured to perform a first injection sequence when pressed against a skin of a patient, the first injection sequence comprising the needle insertion driver being configured to drive a syringe having a needle in a distal direction and the injection driver being configured to drive a syringe stopper in the distal direction to a first stopper position to eject a first fluid portion through the needle,
wherein the reloadable auto injector is configured to perform a second injection sequence when pressed against the skin of the patient, wherein the needle insertion driver is configured to be re-activated upon reloading of the auto injector within the housing, and wherein the reloadable auto injector is configured to perform the second injection sequence after reloading,
the second injection sequence comprising the needle insertion driver being configured to drive the syringe having the needle in the distal direction and the injection driver being configured to drive the syringe stopper in the distal direction from the first stopper position to a second stopper position to eject a second fluid portion through the needle,
wherein the reloadable auto injector is configured to retract the syringe and the injection driver within the housing during reloading.

2. A reloadable auto injector according to claim 1, further comprising:
a plunger rod tube coupled to the needle insertion driver and arranged to drive the syringe in the distal direction, the plunger rod tube comprising a first locking member and a second locking member; and
a plunger rod coupled to the injection driver and movable relative to the plunger rod tube, the plunger rod being configured to advance the syringe stopper, the plunger rod comprising a plunger rod stop to engage with the first locking member and the second locking member;
wherein, when the plunger rod tube is in a first position, the first locking member is in engagement with the plunger rod stop to prevent the plunger rod from advancing, and
wherein, during the first injection sequence, when the plunger rod tube is in a second position, the first locking member is disengaged with the plunger rod stop allowing the plunger rod to be advanced to the first stopper position and wherein the second locking member is in engagement with the plunger rod stop after the first injection sequence to prevent the plunger rod from being further advanced.

3. A reloadable auto injector according to claim 2, wherein, during the second injection sequence, when the plunger rod tube is returned to the second position, the second locking member is disengaged with the plunger rod stop to allow the plunger rod to be advanced to the second stopper position.

4. A reloadable auto injector according to claim 2, further comprising:

a syringe lock comprising a syringe lock guide slot, the syringe lock guide slot having a syringe lock resting ledge;
wherein the plunger rod tube comprises a plunger rod tab being configured to move in the syringe lock guide slot, and
wherein the syringe lock is rotatable relative to the plunger rod tube,
wherein, in a first angular position, the plunger rod tab rests on the syringe lock resting ledge to prevent the plunger rod tube from advancing from the first position, and
wherein, in a second angular position, the plunger rod tab is free of the syringe lock resting ledge to allow the plunger rod tube to advance to the second position, the second position being axially displaced relative to the first position.

5. A reloadable auto injector according to claim 4, further comprising:
the syringe lock being at least partly arranged inside the housing, the plunger rod tube being at least partly arranged inside the syringe lock, and the plunger rod being at least partly arranged inside the plunger rod tube.

6. A reloadable auto injector according to claim 4, wherein the auto injector is configured to rotate the syringe lock to the first angular position between the first and the second injection sequences during reloading of the auto injector.

7. A reloadable auto injector according to claim 4, further comprising a skin sensor configured to interact with the syringe lock to rotate the syringe lock from the first angular position to the second angular position when the skin sensor is activated.

8. A reloadable auto injector according to claim 7, wherein the skin sensor comprises an angled surface configured to engage with a surface of the syringe lock to thereby force the syringe lock to rotate when the skin sensor is activated.

9. A reloadable auto injector according to claim 7, wherein the syringe lock comprises an angled surface configured to engage with a surface of the skin sensor to thereby force the syringe lock to rotate when the skin sensor is activated.

10. A reloadable auto injector according to claim 2, wherein the auto injector is configured to retract the plunger rod tube from the second position to the first position between the first and the second injection sequences during reloading of the auto injector.

11. A reloadable auto injector according to claim 2, wherein, when the plunger rod tube is in the first position after the auto injector is reloaded for the second injection sequence, the second locking member is in engagement with the plunger rod stop to prevent the plunger rod from being further advanced, and
wherein, when the plunger rod tube is in the second position after the auto injector is reloaded, the second locking member is disengaged with the plunger rod stop to allow the plunger rod to advance.

12. A reloadable auto injector according to claim 1 further comprising a reload mechanism configured to manually reload the auto injector.

13. A reloadable auto injector according to claim 2, further comprising a reload handle configured to unlock the first locking member and to release the plunger rod from the plunger rod tube.

14. A reloadable auto injector according to claim 13, further comprising a torsion ring to connect the reload handle with the plunger rod tube.

15. A reloadable auto injector according to claim 14, further comprising a torsion ring tab on the torsion ring to connect the reload handle and the plunger rod tube.

16. A reloadable auto injector comprising:
- a needle insertion driver having a first spring within a housing;
- an injection driver having a second spring within the housing;
- a syringe having a needle within the housing; and
- a syringe stopper,
- the reloadable auto injector configured to perform a first injection sequence when pressed against a skin of a patient, wherein the needle insertion driver is configured to drive the syringe having the needle in a distal direction and the injection driver is configured to drive the syringe stopper in the distal direction to a first stopper position to eject a first fluid portion through the needle, and
- the reloadable auto injector configured to perform a second injection sequence when pressed against the skin of the patient, wherein the needle insertion driver is configured to be re-activated upon a reloading operation of the auto injector using a reload handle to retract the syringe and the injection driver within the housing, wherein the reloadable auto injector is configured to perform the second injection sequence after the reloading operation,
- wherein the second injection sequence includes the needle insertion driver being configured to drive the syringe having the needle in the distal direction and the injection driver being configured to drive the syringe stopper in the distal direction to a second stopper position to eject a second fluid portion through the needle.

\* \* \* \* \*